(12) United States Patent
Fish et al.

(10) Patent No.: US 8,361,144 B2
(45) Date of Patent: Jan. 29, 2013

(54) PERCUTANEOUSLY DELIVERABLE HEART VALVE AND METHODS ASSOCIATED THEREWITH

(75) Inventors: R. David Fish, Houston, TX (US); David Paniagua, Houston, TX (US)

(73) Assignee: Colibri Heart Valve LLC, Broomfield, CO (US)

( * ) Notice: Subject to any disclaimer, the term of this patent is extended or adjusted under 35 U.S.C. 154(b) by 138 days.

(21) Appl. No.: 13/038,361

(22) Filed: Mar. 1, 2011

(65) Prior Publication Data

US 2011/0301700 A1 Dec. 8, 2011

Related U.S. Application Data

(60) Provisional application No. 61/309,109, filed on Mar. 1, 2010.

(51) Int. Cl.
*A61F 2/24* (2006.01)
(52) U.S. Cl. ...... 623/2.11; 623/2.1; 623/2.13; 623/2.17; 435/1.1
(58) Field of Classification Search .................. 623/1.11, 623/1.12, 2.1, 2.11, 2.42, 900, 901, 904, 623/910, 915, 916, 917, 918, 925; 435/1.1
See application file for complete search history.

(56) References Cited

U.S. PATENT DOCUMENTS

| | | | |
|---|---|---|---|
| 3,014,024 A | 12/1961 | Lieberman et al. | |
| 3,029,819 A | 4/1962 | Edward | |
| 3,105,492 A | 10/1963 | Jeckel | |
| 3,320,972 A | 5/1967 | High et al. | |
| 3,409,914 A | 11/1968 | Jones | |
| 3,548,417 A | 12/1970 | Kischer et al. | |
| 3,562,820 A | 2/1971 | Braun | |
| 3,588,920 A | 6/1971 | Wesolowski | |
| 3,671,979 A | 6/1972 | Moulopoulos | |
| 3,878,565 A | 4/1975 | Sauvage | |
| 3,945,052 A | 3/1976 | Liebig | |
| 3,966,401 A | 6/1976 | Hancock et al. | |

(Continued)

FOREIGN PATENT DOCUMENTS

| | | |
|---|---|---|
| WO | 91-17720 | 11/1991 |
| WO | 92-17118 | 10/1992 |

(Continued)

OTHER PUBLICATIONS

Paniagua et al. Abstract 4622: "Percutaneous Implantation of a Low Profile, Dry Membrane, Heart Valve in an Integrated Delivery System in the Aortic and Pulmonary Positions: One-month Animal Results". Circulation. American Heart Association, Inc. 2009; 120: S982.*

(Continued)

*Primary Examiner* — Darwin Erezo
*Assistant Examiner* — Shaun L David
(74) *Attorney, Agent, or Firm* — Fox Rothschild LLP

(57) ABSTRACT

A prosthetic heart valve implantable by catheter without surgery includes a substantially "dry" membrane or tissue material. In at least one embodiment, the tissue is folded in a dry state to form a tissue leaflet assembly that is then attached to a frame to form an implantable prosthetic heart valve. Alternatively, one or more tissue leaflets are operatively associated with a frame to form an implantable prosthetic heart valve. The implantable prosthetic heart valve is subsequently premounted on an integrated catheter delivery system. The catheter delivery system that includes the implantable prosthetic heart valve is then packaged and transported while the tissue remains dry. The implantable prosthetic heart valve, while remaining substantially dry, can then be implanted into the receiving patient.

38 Claims, 25 Drawing Sheets

U.S. PATENT DOCUMENTS

| | | | |
|---|---|---|---|
| 3,986,828 A | 10/1976 | Hoffman, Jr. et al. |
| 4,035,849 A | 7/1977 | Angell et al. |
| 4,056,854 A | 11/1977 | Boretos et al. |
| 4,060,081 A | 11/1977 | Yannas et al. |
| 4,082,507 A | 4/1978 | Sawyer |
| 4,084,268 A | 4/1978 | Ionescu et al. |
| 4,164,045 A | 8/1979 | Bokros et al. |
| 4,172,295 A | 10/1979 | Batten |
| 4,218,782 A | 8/1980 | Rygg |
| 4,222,126 A | 9/1980 | Boretos et al. |
| 4,265,694 A | 5/1981 | Boretos et al. |
| 4,291,420 A | 9/1981 | Reul |
| 4,350,492 A | 9/1982 | Wright et al. |
| 4,364,127 A | 12/1982 | Pierce et al. |
| 4,388,735 A | 6/1983 | Ionescu et al. |
| 4,441,216 A | 4/1984 | Ionescu et al. |
| 4,456,589 A | 6/1984 | Holman et al. |
| 4,473,423 A | 9/1984 | Kolff |
| 4,477,930 A | 10/1984 | Totten et al. |
| 4,517,687 A | 5/1985 | Liebig et al. |
| 4,545,082 A | 10/1985 | Hood |
| 4,597,762 A | 7/1986 | Walter et al. |
| 4,600,533 A | 7/1986 | Chu |
| 4,631,052 A | 12/1986 | Kensey |
| 4,666,442 A | 5/1987 | Arru et al. |
| 4,728,328 A | 3/1988 | Hughes et al. |
| 4,759,758 A | 7/1988 | Gabbay |
| 4,798,611 A | 1/1989 | Freeman, Jr. |
| 4,801,299 A | 1/1989 | Brendel et al. |
| 4,870,966 A | 10/1989 | Dellon et al. |
| 4,883,458 A | 11/1989 | Shiber |
| 4,892,539 A | 1/1990 | Koch |
| 4,966,604 A | 10/1990 | Reiss |
| 4,976,733 A | 12/1990 | Girardot |
| 4,979,939 A | 12/1990 | Shiber |
| 5,007,896 A | 4/1991 | Shiber |
| 5,011,488 A | 4/1991 | Ginsburg |
| 5,026,366 A | 6/1991 | Leckrone |
| 5,032,128 A | 7/1991 | Alonso |
| 5,047,041 A | 9/1991 | Samuels |
| 5,047,050 A | 9/1991 | Arpesani |
| 5,052,771 A | 10/1991 | Williams et al. |
| 5,080,660 A | 1/1992 | Buelna |
| 5,139,515 A | 8/1992 | Robicsek |
| 5,163,955 A | 11/1992 | Love et al. |
| 5,171,273 A | 12/1992 | Silver et al. |
| 5,226,889 A | 7/1993 | Sheiban |
| 5,261,878 A | 11/1993 | Galindo |
| 5,282,847 A | 2/1994 | Trescony et al. |
| 5,326,370 A | 7/1994 | Love et al. |
| 5,326,371 A | 7/1994 | Love et al. |
| 5,332,402 A | 7/1994 | Teitelbaum |
| 5,336,616 A | 8/1994 | Livesey et al. |
| 5,360,443 A | 11/1994 | Barone et al. |
| 5,374,539 A | 12/1994 | Nimni et al. |
| 5,376,110 A | 12/1994 | Tu et al. |
| 5,383,927 A | 1/1995 | De Goicoechea et al. |
| 5,413,601 A | 5/1995 | Keshelava |
| 5,476,506 A | 12/1995 | Lunn |
| 5,480,424 A | 1/1996 | Cox |
| 5,500,015 A | 3/1996 | Deac |
| 5,509,930 A | 4/1996 | Love |
| 5,522,879 A | 6/1996 | Scopelianos |
| 5,522,881 A | 6/1996 | Lentz |
| 5,545,215 A | 8/1996 | Duran |
| 5,549,664 A | 8/1996 | Hirata et al. |
| 5,549,666 A | 8/1996 | Hata et al. |
| 5,571,170 A | 11/1996 | Palmaz et al. |
| 5,571,173 A | 11/1996 | Parodi |
| 5,571,174 A | 11/1996 | Love et al. |
| 5,578,071 A | 11/1996 | Parodi |
| 5,578,072 A | 11/1996 | Barone et al. |
| 5,582,168 A | 12/1996 | Samuels et al. |
| 5,591,229 A | 1/1997 | Parodi |
| 5,634,928 A | 6/1997 | Fischell et al. |
| 5,653,749 A | 8/1997 | Love et al. |
| 5,713,953 A | 2/1998 | Vallana et al. |
| 5,728,152 A | 3/1998 | Mirsch, II et al. |
| 5,733,299 A | 3/1998 | Sheiban et al. |
| 5,741,333 A | 4/1998 | Frid |
| 5,746,775 A | 5/1998 | Levy et al. |
| 5,769,780 A | 6/1998 | Hata et al. |
| 5,782,914 A | 7/1998 | Schankereli |
| 5,787,887 A | 8/1998 | Klingenbeck-Regn |
| 5,840,081 A | 11/1998 | Anderson et al. |
| 5,855,601 A | 1/1999 | Bessler et al. |
| 5,861,028 A | 1/1999 | Angell |
| 5,862,806 A | 1/1999 | Cheung |
| 5,895,420 A | 4/1999 | Mirsch, II et al. |
| 5,957,949 A | 9/1999 | Leonhardt et al. |
| 5,961,539 A | 10/1999 | Northrup et al. |
| 5,961,549 A | 10/1999 | Nguyen et al. |
| 5,972,030 A | 10/1999 | Garrison et al. |
| 5,976,179 A | 11/1999 | Inoue |
| 6,004,328 A | 12/1999 | Solar |
| 6,010,531 A | 1/2000 | Donlon et al. |
| 6,029,671 A | 2/2000 | Stevens et al. |
| 6,053,938 A | 4/2000 | Goldmann et al. |
| 6,091,984 A | 7/2000 | Perelman et al. |
| 6,102,944 A | 8/2000 | Huynh et al. |
| 6,117,169 A | 9/2000 | Moe |
| 6,125,852 A | 10/2000 | Stevens et al. |
| 6,126,686 A | 10/2000 | Badylak et al. |
| 6,129,756 A | 10/2000 | Kugler |
| 6,162,245 A | 12/2000 | Jayaraman |
| 6,168,619 B1 | 1/2001 | Dihn et al. |
| 6,174,327 B1 | 1/2001 | Mertens et al. |
| 6,197,143 B1 | 3/2001 | Bodnar |
| 6,214,055 B1 | 4/2001 | Simionescu et al. |
| 6,221,091 B1 | 4/2001 | Khosravi |
| 6,254,629 B1 | 7/2001 | Inoue |
| 6,254,630 B1 | 7/2001 | Inoue |
| 6,254,636 B1 | 7/2001 | Peredo |
| 6,264,691 B1 | 7/2001 | Gabbay |
| 6,269,819 B1 | 8/2001 | Oz et al. |
| 6,270,526 B1 | 8/2001 | Cox |
| 6,277,397 B1 | 8/2001 | Shimizu |
| 6,277,555 B1 | 8/2001 | Duran et al. |
| 6,287,335 B1 | 9/2001 | Drasler et al. |
| 6,312,462 B1 | 11/2001 | McDermott et al. |
| 6,312,474 B1 | 11/2001 | Francis et al. |
| 6,342,069 B1 | 1/2002 | Deac et al. |
| 6,352,554 B2 | 3/2002 | De Paulis |
| 6,352,708 B1 | 3/2002 | Duran et al. |
| 6,358,275 B1 | 3/2002 | McIlroy et al. |
| 6,358,284 B1 | 3/2002 | Fearnot et al. |
| 6,378,221 B1 | 4/2002 | Ekholm, Jr. et al. |
| 6,383,171 B1 | 5/2002 | Gifford et al. |
| 6,391,333 B1 | 5/2002 | Li et al. |
| 6,409,755 B1 | 6/2002 | Vrba |
| 6,418,339 B1 | 7/2002 | Essenpreis et al. |
| 6,425,916 B1 | 7/2002 | Garrison et al. |
| 6,432,712 B1 | 8/2002 | Wolfinbarger, Jr et al. |
| 6,440,167 B2 | 8/2002 | Shimizu |
| 6,458,153 B1 | 10/2002 | Bailey et al. |
| 6,468,313 B1 | 10/2002 | Claeson et al. |
| 6,471,723 B1 | 10/2002 | Ashworth et al. |
| 6,482,227 B1 | 11/2002 | Solovay |
| 6,482,228 B1 | 11/2002 | Norred |
| 6,482,240 B1 | 11/2002 | Echmayer et al. |
| 6,491,719 B1 | 12/2002 | Fogarty et al. |
| 6,494,909 B2 | 12/2002 | Greenhalgh |
| 6,534,004 B2 * | 3/2003 | Chen et al. ............ 422/40 |
| 6,553,681 B2 | 4/2003 | Ekholm, Jr. et al. |
| 6,565,960 B2 | 5/2003 | Koob et al. |
| 6,569,200 B2 | 5/2003 | Wolfinbarger, Jr. et al. |
| 6,582,464 B2 * | 6/2003 | Gabbay ............ 623/2.38 |
| 6,599,524 B2 | 7/2003 | Li et al. |
| 6,624,890 B2 | 9/2003 | Backman et al. |
| 6,626,938 B1 | 9/2003 | Butaric et al. |
| 6,652,577 B2 | 11/2003 | Gianotti |
| 6,652,578 B2 | 11/2003 | Bailey et al. |
| 6,666,886 B1 | 12/2003 | Tranquillo et al. |
| 6,682,559 B2 | 1/2004 | Myers et al. |
| 6,696,074 B2 | 2/2004 | Dai et al. |
| 6,702,826 B2 | 3/2004 | Liddicoat et al. |
| 6,719,788 B2 | 4/2004 | Cox |

| | | |
|---|---|---|
| 6,719,789 B2 | 4/2004 | Cox |
| 6,736,823 B2 | 5/2004 | Darios et al. |
| 6,764,510 B2 | 7/2004 | Vidlund et al. |
| 6,773,456 B1 | 8/2004 | Gordon et al. |
| 6,773,457 B2 | 8/2004 | Ivancev |
| 6,790,229 B1 | 9/2004 | Berreklouw |
| 6,792,979 B2 | 9/2004 | Konya et al. |
| 6,802,319 B2 | 10/2004 | Gifford, III et al. |
| 6,821,530 B2 | 11/2004 | Koob et al. |
| 6,908,481 B2 | 6/2005 | Cribier |
| 6,913,608 B2 | 7/2005 | Liddicoat et al. |
| 6,916,338 B2 | 7/2005 | Speziali |
| 6,942,694 B2 | 9/2005 | Liddicoat et al. |
| 6,951,571 B1 | 10/2005 | Srivastava |
| 6,961,123 B1 | 11/2005 | Wang et al. |
| 6,977,231 B1 | 12/2005 | Matsuda |
| 6,986,735 B2 | 1/2006 | Abraham et al. |
| 7,008,763 B2 | 3/2006 | Cheung |
| 7,011,688 B2 | 3/2006 | Gryska et al. |
| 7,018,404 B2 | 3/2006 | Holmberg et al. |
| 7,022,348 B2 | 4/2006 | Ketharananthan |
| 7,037,333 B2 | 5/2006 | Myers et al. |
| 7,039,446 B2 | 5/2006 | Ruchti et al. |
| 7,041,132 B2 | 5/2006 | Quijano et al. |
| 7,053,051 B2 | 5/2006 | Hendriks et al. |
| 7,060,092 B2 | 6/2006 | Kuribayashi et al. |
| 7,077,862 B2 | 7/2006 | Vidlund et al. |
| 7,084,082 B1 | 8/2006 | Shimizu |
| 7,138,226 B2 | 11/2006 | Vincek et al. |
| 7,153,324 B2 | 12/2006 | Case et al. |
| 7,164,145 B2 | 1/2007 | Shakespeare |
| 7,166,570 B2 | 1/2007 | Hunter et al. |
| 7,189,259 B2 | 3/2007 | Simionescu et al. |
| 7,213,601 B2 | 5/2007 | Stevens et al. |
| 7,214,242 B2 | 5/2007 | Abraham et al. |
| 7,232,461 B2 | 6/2007 | Ramer |
| 7,261,732 B2 | 8/2007 | Justino |
| 7,289,211 B1 | 10/2007 | Walsh, Jr. et al. |
| 7,309,461 B2 | 12/2007 | Kujawski et al. |
| 7,318,998 B2 | 1/2008 | Goldstein et al. |
| 7,329,279 B2 | 2/2008 | Haug et al. |
| 7,331,993 B2 | 2/2008 | White |
| 7,354,702 B2 | 4/2008 | Dai et al. |
| RE40,404 E | 6/2008 | Schmitt et al. |
| 7,381,218 B2 | 6/2008 | Schreck |
| 7,381,219 B2 | 6/2008 | Salahieh et al. |
| 7,427,291 B2 | 9/2008 | Liddicoat et al. |
| 7,431,725 B2 | 10/2008 | Stack et al. |
| 7,481,838 B2 | 1/2009 | Carpentier et al. |
| 7,510,571 B2 | 3/2009 | Spiridigliozzi et al. |
| 7,510,575 B2 | 3/2009 | Spenser et al. |
| 7,524,330 B2 | 4/2009 | Berreklouw |
| 7,566,343 B2 | 7/2009 | Jenson et al. |
| 7,585,321 B2 | 9/2009 | Cribier |
| 7,604,661 B2 | 10/2009 | Pavcnik et al. |
| 7,622,276 B2 | 11/2009 | Cunanan et al. |
| 7,648,676 B2 | 1/2010 | Mills et al. |
| 8,007,992 B2 * | 8/2011 | Tian et al. ............... 435/1.1 |
| 2001/0010017 A1 | 7/2001 | Letac et al. |
| 2001/0023372 A1 | 9/2001 | Chen et al. |
| 2001/0049558 A1 | 12/2001 | Liddicoat et al. |
| 2002/0005073 A1 | 1/2002 | Tompkins et al. |
| 2002/0028243 A1 | 3/2002 | Masters |
| 2002/0029783 A1 | 3/2002 | Stevens et al. |
| 2002/0037940 A1 | 3/2002 | Koob et al. |
| 2002/0042621 A1 | 4/2002 | Liddicoat et al. |
| 2002/0091441 A1 | 7/2002 | Guzik |
| 2002/0095167 A1 | 7/2002 | Liddicoat et al. |
| 2002/0095994 A1 | 7/2002 | Vesely et al. |
| 2002/0128708 A1 | 9/2002 | Northrup et al. |
| 2003/0078659 A1 | 4/2003 | Yang |
| 2003/0102000 A1 | 6/2003 | Stevens et al. |
| 2003/0130727 A1 | 7/2003 | Drasler et al. |
| 2003/0130729 A1 | 7/2003 | Paniagua et al. |
| 2003/0130731 A1 | 7/2003 | Vidlund et al. |
| 2003/0153974 A1 | 8/2003 | Spenser et al. |
| 2003/0187362 A1 | 10/2003 | Murphy et al. |
| 2003/0204023 A1 | 10/2003 | Koob et al. |
| 2003/0212460 A1 | 11/2003 | Darois et al. |
| 2003/0212462 A1 | 11/2003 | Gryska et al. |
| 2003/0217415 A1 | 11/2003 | Crouch et al. |
| 2004/0024452 A1 | 2/2004 | Kruse et al. |
| 2004/0055608 A1 | 3/2004 | Stevens et al. |
| 2004/0059418 A1 | 3/2004 | McKay et al. |
| 2004/0098092 A1 | 5/2004 | Butaric et al. |
| 2004/0193261 A1 | 9/2004 | Berreklouw |
| 2004/0243153 A1 | 12/2004 | Liddicoat et al. |
| 2004/0243229 A1 | 12/2004 | Vidlund et al. |
| 2005/0027369 A1 | 2/2005 | Eldridge et al. |
| 2005/0043819 A1 | 2/2005 | Schmidt et al. |
| 2005/0096673 A1 | 5/2005 | Stack et al. |
| 2005/0113910 A1 | 5/2005 | Paniagua et al. |
| 2005/0142163 A1 | 6/2005 | Hunter et al. |
| 2005/0147562 A1 | 7/2005 | Hunter et al. |
| 2005/0147599 A1 | 7/2005 | Hunter et al. |
| 2005/0147643 A1 | 7/2005 | Hunter et al. |
| 2005/0148512 A1 | 7/2005 | Hunter et al. |
| 2005/0158274 A1 | 7/2005 | Hunter et al. |
| 2005/0159811 A1 | 7/2005 | Lane |
| 2005/0169958 A1 | 8/2005 | Hunter et al. |
| 2005/0169959 A1 | 8/2005 | Hunter et al. |
| 2005/0175657 A1 | 8/2005 | Hunter et al. |
| 2005/0187618 A1 | 8/2005 | Gabbay |
| 2005/0191248 A1 | 9/2005 | Hunter et al. |
| 2005/0246035 A1 | 11/2005 | Wolfinbarger, Jr et al. |
| 2005/0247320 A1 | 11/2005 | Stack et al. |
| 2005/0267529 A1 | 12/2005 | Crockett et al. |
| 2006/0004439 A1 | 1/2006 | Spenser et al. |
| 2006/0004443 A1 | 1/2006 | Liddicoat et al. |
| 2006/0020336 A1 | 1/2006 | Liddicoat |
| 2006/0025800 A1 | 2/2006 | Suresh |
| 2006/0041306 A1 | 2/2006 | Vidlund et al. |
| 2006/0074486 A1 | 4/2006 | Liddicoat et al. |
| 2006/0111733 A1 | 5/2006 | Shriver |
| 2006/0129225 A1 | 6/2006 | Kopia et al. |
| 2006/0134079 A1 | 6/2006 | Sih et al. |
| 2006/0140916 A1 | 6/2006 | Siani-Rose et al. |
| 2006/0178740 A1 | 8/2006 | Stacchino et al. |
| 2006/0193885 A1 | 8/2006 | Neethling et al. |
| 2006/0195010 A1 | 8/2006 | Arnal et al. |
| 2006/0195183 A1 | 8/2006 | Navia et al. |
| 2006/0240063 A9 | 10/2006 | Hunter et al. |
| 2006/0240064 A9 | 10/2006 | Hunter et al. |
| 2006/0259134 A1 | 11/2006 | Schwammenthal et al. |
| 2006/0259135 A1 | 11/2006 | Navia et al. |
| 2006/0259137 A1 | 11/2006 | Artof et al. |
| 2006/0265056 A1 | 11/2006 | Nguyen et al. |
| 2006/0287571 A1 | 12/2006 | Gozzi et al. |
| 2006/0292125 A1 | 12/2006 | Kellar et al. |
| 2007/0010857 A1 | 1/2007 | Sugimoto et al. |
| 2007/0050014 A1 | 3/2007 | Johnson |
| 2007/0050022 A1 | 3/2007 | Vidlund et al. |
| 2007/0060932 A1 | 3/2007 | Stack et al. |
| 2007/0128174 A1 | 6/2007 | Kleinsek et al. |
| 2007/0173861 A1 | 7/2007 | Strommer et al. |
| 2007/0213813 A1 | 9/2007 | Von Segessler et al. |
| 2007/0263226 A1 | 11/2007 | Kurtz et al. |
| 2007/0276432 A1 | 11/2007 | Stack et al. |
| 2008/0009667 A1 | 1/2008 | Longhini et al. |
| 2008/0009940 A1 | 1/2008 | Cribier |
| 2008/0029105 A1 | 2/2008 | Stevens et al. |
| 2008/0039871 A1 | 2/2008 | Wallace et al. |
| 2008/0039926 A1 | 2/2008 | Majercak et al. |
| 2008/0058798 A1 | 3/2008 | Wallace et al. |
| 2008/0082113 A1 | 4/2008 | Bishop et al. |
| 2008/0102439 A1 | 5/2008 | Tian et al. |
| 2008/0133004 A1 | 6/2008 | White |
| 2008/0147182 A1 | 6/2008 | Righini et al. |
| 2008/0154356 A1 | 6/2008 | Obermiller et al. |
| 2008/0177381 A1 | 7/2008 | Navia et al. |
| 2008/0183283 A1 | 7/2008 | Downing |
| 2008/0190989 A1 | 8/2008 | Crews et al. |
| 2008/0195200 A1 | 8/2008 | Vidlund et al. |
| 2008/0200977 A1 | 8/2008 | Paul et al. |
| 2009/0030511 A1 * | 1/2009 | Paniagua et al. ............ 623/2.13 |
| 2009/0062907 A1 | 3/2009 | Quijano et al. |
| 2009/0164005 A1 * | 6/2009 | Dove et al. ................. 623/2.13 |
| 2009/0187241 A1 | 7/2009 | Melsheimer |

| | | | |
|---|---|---|---|
| 2009/0248149 | A1 | 10/2009 | Gabbay |
| 2009/0254175 | A1 | 10/2009 | Quijano et al. |
| 2010/0161036 | A1 | 6/2010 | Pintor et al. |
| 2010/0234878 | A1 | 9/2010 | Hruska |
| 2010/0256749 | A1 | 10/2010 | Tran et al. |
| 2011/0300625 | A1 | 12/2011 | Paniagua et al. |
| 2011/0301700 | A1 | 12/2011 | Fish et al. |
| 2012/0158128 | A1* | 6/2012 | Gautam et al. ............... 623/2.11 |

FOREIGN PATENT DOCUMENTS

| | | |
|---|---|---|
| WO | 99/30646 | 6/1999 |
| WO | 01-02031 | 1/2001 |
| WO | 03-092554 | 11/2003 |
| WO | 2006-095342 | 9/2006 |
| WO | 2007-138572 | 12/2007 |
| WO | 2009-052188 | 4/2009 |
| WO | 2009-156471 | 12/2009 |
| WO | 2011-109433 | 3/2011 |
| WO | 2011-109450 | 9/2011 |
| WO | 2012-006124 | 1/2012 |

OTHER PUBLICATIONS

PCT International Search Report and Written Opinion, in Application PCT/US2011/042252, dated Apr. 6, 2011.
PCT International Search Report and Written Opinion, in Application PCT/US2011/053120, dated Apr. 27, 2012.
Affidavit of Dr. Paolo Angelini, M.D., signed Aug. 25, 2009.
Affidavit of Dr. Gervasio A. Lamas, M.D., signed Sep. 3, 2009.
Andersen, H.R. et al., "Transluminal implantation of artificial heart valve" European Heart Journal, 1992, 13, pp. 704-708.
"Artificial heart valve" http://en.wikipedia.org/Artificial_heart_valve, printed May 13, 2009.
Bonhoeffer, Philipp M.D. et al., "Percutaneous Insertion of the Pulmonary Valve" J of the Amer College of Cardiology, vol. 39, No. 10, Elsevier Science, Inc. 2002, pp. 1664-1669, London, UK, and Paris, FR.
Bonhoeffer, Philipp et al., "Percutaeous replacement of pulmonary valve in a right-centricle to pulmonary-artery prosthetic conduit with valve dysfunction" Early Report, The Lacet, vol. 356, Oct. 21, 2000, p. 1403-1405.
Bonhoeffer, Philipp et al., "Transcatherter Implantation of a Bovine Valve in Pulmonary Position: A Lamb Study" Circulation J. of the Amer Heart Assoc, 2000; 102; 813-816.
Boudjemline, Younes et al., "Percutaneous pulmonary valve replacement in a large right ventricular outflow tract: An experimental study" J. Am. Coll. Cardiol. 2004; 43; 1082-1087.
Braga-Vilela, A. et al., "Extracellular Matrix of Porcine Pericardium; Biochemistry and Collagen Architecture" J. Membr Biol., 2008.
Breuer, Christopher K. M.D. et al., "Application of Tissue-Engineering Principles toward the Development of a Semilunar Heart Valve Substitute" Tissue Engineering, vol. 10, No. 11/12, 2004 pp. 1725-1736.
Cale, A.R. et al., "Revisited: a descending thorasic aortic valve to treat prosthetic valve insufficiency" Ann Thorac Surg, May 1993, 55(5), pp. 1218-2.
Cerrolaza, M et al., "A comparison of the hydrodynamical behaviour of three heart aortic prostheses by numerical methods".
"Collagen" http://en.wikipedia.org/wiki/Collagen, printed May 13, 2009.
Collins, J. J., Jr, "The Evolution of artificial heart valve" N. Engl J Med, Feb. 28, 1991; 324(9):624-6.
Corden, J. et al., "The influence of open leaflet geometry on the haemodynamic flow characteristics of polyrethane trileaflet artificial heart valve" PubMed medline query, p. 1 of 1.
Cribier, Alain et al., "Percutaneious Transcatheter Implantation of an Aoritc Valve Prosthesis for Calcific Aortic Stenosis: First Human Case Description" Circulation J of the Amer Heart Assoc, originally published online Nov. 25, 2002.
Edwards Lifesciences Receives FDA Approval for New Heart Valve, http:www.medicalnewstoday.com/articles/149588.php, dated May 11, 2009.
Fish, R. David, "Percutaneous Heart Valve Replacement: Enthusiasm Tempered" Circulation J of the Amer Heart Assoc, 2004; 110; 1876-1878.

Fishbein, M.C. et al., "Cardiac pathology after aortic valve replacement using Hufnagel trileaflet prostheses: study of 20 necropsy patients" Ann Heart J., Apr. 1975, 89(4), pp. 443-448.
Gloeckner, D. Claire et al., "Mechanical Evaluation and Design of a Multilayered Collagenous Repair Biomaterial" J. of Biomedical Materials Research Part A, vol. 52 Iss 2, pp. 365-373, Published online Aug. 15, 2000, Wiley Periodicals, Inc.
Grube E., et al., "Progress and Current Status of Percutaneous Aortic Valve Replacement: Results of Three Device Generations of the CoreValve Revalving System", Circ. Cardiovasc Intervent. 2008;1:167-175 (abstract).
Hanlon, JG et al., "Pre-use intraoperative testing of autologous tissue for valvular surgery: a proof of concept study" J. Heart Valve Dis, Nov. 1999; 8(6); pp. 614-623.
Bech-Hanssen, Odd, M.D. et al., "Aortic Prosthetic Valve Desing and Size: Relation to Doppler Echocardiographic Finding and Pressure Recovery—An in Vitro Study" J. Am Soc Echocardiography 2000; 13:39-50.
Hasenkam, J.M. et al., "A model for acute haemodynamic studies in the ascending aorta in pigs" Cardiovasc Res, Jul. 1988, 22(7), pp. 464-471.
Hiester,E.D. et al., "Optimal bovine pericardial tissue selection sites. I. Fiber architecture and tissue thickness measurements." J. Biomed Mater Res, 1998, Feb. 2001; 39(2):207-14.
Hufnagel, Charles A., M.D., "Basic Concepts in the Development of Cardiovascular Prosthes" The American Journal of Surgery, vol. 137, Mar. 1979.
Hufnagel, Charles.A., MD et al., "In the beginning. Surgical Correction of Aortic Insufficiency" 1954; Ann Thorac Surg May 1989; 47(3), pp. 475-476.
Hufnagel, Charles.A., MD et al., "Late follow-up of ball-valve prostheses in the descending thoracic aortia", J. Throrac Cardiovasc Surg, Dec. 1976, 72(6), pp. 900-909.
Hufnagel, Charles.A., MD et al., "Surgical Correction of Aortic Insufficiency" Surgery vol. 35, May 1954, No. 5.
Hufnagel, Charles A., "Vessels and Valves", Sec. 1: Development of Cardiac Surgery, Chap 7, pp. 43-55.
"Introduction to Stereomicroscopy", http://www.microscopyu.com/articles/stereomicroscopy/stereointro.html, May 13, 2009.
IOPATCH(R) Tutoplast(R) Processed Pericardium Directions for Use; http://www.iopinc.com/surgeons_and_medical_professionals/iopatch/directions.asp, printed on Jun. 2, 2009.
Knudsen, LL et al., "Catheter-implanted prosthetic heart valves. Transluminal catheter implantation of a new expandable artificial heart valve in the descending thoracic aorta in isolated vessels and closed chest pigs" Int J. Artif Organs, May 1993, 16(5); pp. 253-262.
Lax, Jorge A., M.D., et al. "Estimation of the Ejection Fraction in Patients with Myocardial Infarction Obtained from the Combined Index of Systolic and Diastolic Left Ventricular Function: A New Method" J of the American Soc of Echocardiography, vol. 13, No. 2.
Liao, Jun et al., "Molecular orientation of collagen in intact planar connective tissues under biaxial stretch" Acta Biomateriala, vol. 1, Iss. 1, Jan. 2005, pp. 45-54.
Liao, K X et al., "Two-dimensional mechanical and ultrastructural correlates of bovine pericardium for prosthetic valves" ASAIO Trans, Jun. 1, 1991, 37(3); M341-51.
LS, Yu et al., "New Polyurethane valves in new soft artificial heart" ASAIO Trans Jul.-Sep. 1989; 35(3), pp. 301-304.
Mirnajafi, A. et al. "The effects of collagen fiber orientation of the flexural properties of pericardial heterograft biomaterials" Biomaterials, Mar. 2005; 26(7): 795-804.
Mirzaie, M. et al., "A new storage solution for porcine aortic valves" Ann Thorac Cardiovasc Surg. Apr. 2007;13(2):102-9.
Moazami, N. et al., "Transluminal aortic valve placement. A feasibility study with a newly designed collapsible aortic valve" ASAIO J, Sep.-Oct. 1996, 42(5):M 381-5.
Nienaber C., M.D. et al., "Nonsurgical Reconstruction of Thoracic Aortic Dissection by Stent-Graft Placement" N. Eng. J. Med, May 20, 1999, col. 340, No. 20.
Noorlander, Maril L. et al., "A Quantitative Method to Determine the Orientation of Collagen Fibers in the Dermis" The J. Of Histochemistry & Cytochemistry, vol. 50(11): 2002, pp. 1469-1474.

Nunn, D.B., "Structural Failure of Dacron Arterial Grafts" Seminars in Vascular Surgery, col. 12, No. 1 (Mar. 1999), pp. 88-91.

Optical Microscope, Wikipedia, http://en.wikipedia.org/wiki/Stereomiscroscope, May 13, 2009.

Orthogonality, http://en.wikipedia.org/wiki/Orthogonal, May 13, 2009.

Paniagua, David, et al., Percutaneous Heart Valve in the Chronic in Vitro Testing Model, Circulation, 2002, pp. e51-52, vol. 106, American Heart Association, US.

Paniagua, David et al., First Human Case of Retrograde Transcatheter Implantation of an Aortic Valve Prosthesis, Texas Heart Institute Journal, 2005, pp. 91-96, vol. 32, US.

Pathak, CP et al., "Treatment of bioprosthetic heart valve tissue with long chain alcohol solution to lowercalcification potential""J Biomed Mater Res A. Apr. 1, 2004;69(1):140-4".

Pavenik, Susan, M.D., PhD et al., "Development and Initial Experimental Evaluation of a Prosthetic Aortic Valve for Transcatherter Placement" Cardivascular Radiology, Apr. 1992, pp. 151-154.

Pick, Adam, "True or False: An Edwards Lifescience' Tissue Valve Replacement Requires 1,800 Hand-Sewn Stitches" http://heart-valve-surgery.com/heart-surgery-blog/2008/02/26. printed Aug. 13, 2010.

Pohl, M. et al., "In vitro testing of artificial heart valves; comparison between Newtonian and non-Newtonian fluids" Artif Argns, Jan. 1996; 20(1); pp. 37-46.

Purinya, B. et al., "Biomechanical and Structural Properties of the Explanted Bioprosthetic Valve Leaflets" J. of Biomechanis, vol. 27, Iss 1, Jan. 1994 pp. 1-11 Elsevier Science Ltd, 1993.

Sacks, M S et al., "Collagen fiber architecture of bovine pericardium" ASAIO J, Jul. 1, 1994, 40(3):M632-7.

Sacks, M S et al., "A small angle light scattering device for planar connective tissue miscrostructural analysis" Ann Biomed Eng, Jul. 1, 1997, 254(4); 678-89.

Sacks, Michael S, "Incorporation of experimentally-derived fiber orientation into a structural constitutive model for planar collagenous tissues" J. Biomech Eng, Apr. 1, 2003, 125(2); 280-7.

Sacks, Michael S. et al., "Quantification of the fiber architecture and biaxial mechanical behavior of porcine intestinal submucosa" J of Biomedical Research, vol. 46, Iss 1, Jul. 1999, pp. 1-10.

Samouillan, V. et al., "Comparison of chemical treatments on the chain dynamics and thermal stability of bovine pericardium collagen" J Biomed Mater Res A. Feb. 1, 2003; 64(2):330-8.

Schoen, Frederick J., "Tissue heart valves: Current challenges and future research perspectives" J of Biomedical Materials Research, vol. 47, Iss 4, Dec. 15, 1999, pp. 439-465.

Sellaro, Tiffany L., "Effects of Collagen Orientation on the Medium-Term Fatigue Response of Heart Valve Biomaterials" 2003, (published thesis) pp. 40-45.

Sellaro, Tiffany L. et al., "Effects of Collagen Fiber Orientation on the Response of Biologically Derived Soft Tissue Biomaterials to Cyclic Loading" J. Biomed Mater Res A 2007, Jan. 1; 80(1): 194-205); published online Oct. 13, 2006 by Wiley InterScience.

Shandas, Robin PhD et al., "A Method for Determining the Reference Effective Flow Areas for Mechanical Heart Valve Prostheses" Circulation Apr. 25, 2000.

Shen, Ming et al., "Effect of ethanol and ether in the prevention of calcification of bioprostheses" Ann Thorac Surg. May 2001;71(5 Suppl):S413-6.

Shen, Ming et al., "Protein adsorption in glutaraldehyde-preserved bovine pericardium and porcine valve tissues" The Annals of Thoracic Surgery, 2001; 71:409-409.

Simionescu, D et al., "Mapping of glutaraldehyde-treated bovine pericardium and tissue selection for bioprosthetic heart valve" J. Biomed Mater Res, Jun. 1, 1993:27(6):697-704.

Sun, Wei et al., "Response of heterograft heart valve biomaterials to moderate cyclic loading" J Biomed Mater Res A, Jun. 2004, 69(4); 658-69.

Topol, Eric J., "Textbook of Interventional Cardiology", 1990, Chs. 43-44, pp. 831-867.

Vyavahare, Narendra et al., "Mechanisms of bioprosthetic heart valve failure: Fatigue causes collagen denaturation and glycosaminoglysan loss" J of Biomedical Research, vol. 446, Iss 1, Jul. 1999, pp. 44-50.

Vyavahare, NR et al., "Prevention of Glutaraldehyde-Fixed Bioprosthetic Heart Valve Calcification by Alcohol Pretreatment: Further Mechanistic Studies" J Heart Valve Dis. Jul. 2000;9(4):561-6.

Werner, S. et al., "Testing the Hydrodynamic properties of heart valve prostheses with a new test apparatus", Biomed Tech (Berl) Sep. 1994; 30(9); pp. 204-210.

Wiegner, A W et al., "Mechanical and structural correlates of canine pericardium" Circ Res, Sep. 1, 1981m 49(3); 807-14.

Yasui, Takeshi et al., "Determination of collagen fiber orientation in human tissue by use of polarization measurement of molecular second-harmonic-generation light", Applied Optics, vol. 42, No. 14, May 10, 2004, pp. 2861-2867.

Zioupos, P. et al., "Anisotropic Elasticity and Strength of Glutaraldehyde Fixed Bovine Pericardium for Use in Pericardial Bioprosthetic Valves" J. Biomed Mater Res., Jan. 1994, 28(1):49-57.

Zioupos, P. et al., "Mechanical and Optical anisotrophy of bovine pericardium" Med Biol Eng Comput, Jan. 1992; 30(1); pp. 76-82.

Supplemental Declaration Under 37 CFR 1.131 by inventors filed in U.S. Appl. No. 10/887,688, filed Dec. 15, 2008.

Office Action issued in U.S. Appl. No. 10/887,688, dated Nov. 28, 2007.

Final Office Action issued in U.S. Appl. No. 10/887,688, dated Jul. 15, 2008.

Office Action issued in U.S. Appl. No. 10/887,688, dated Mar. 16, 2009.

Examiner Interview Summary issued in U.S. Appl. No. 10/887,688, dated Jun. 12, 2009.

Final Office Action issued in U.S. Appl. No. 10/887,688, dated Mar. 2, 2010.

Supplemental Declaration Under 37 CFR 1.131 by inventors filed in U.S. Appl. No. 10/887,688, filed Sep. 14, 2009.

Supplemental Declaration Under 37 CFR 1.131 by inventors filed in U.S. Appl. No. 10/887,688, filed Feb. 28, 2008.

Examiner Interview Summary issued in U.S. Appl. No. 10/887,688, dated Jul. 26, 2010.

Office Action issued in U.S. Appl. No. 10/887,688, dated Feb. 12, 2012.

Office Action issued Sep. 29, 2010, issued in U.S. Appl. No. 12/228,192.

Examiner Interview Summary, dated Apr. 5, 2011 in U.S. Appl. No. 12/228,192.

Final Office Action issued Jul. 14, 2011, in U.S. Appl. No. 12/228,192.

Office Action issued in U.S. Appl. No. 10/037,266, dated May 8, 2003.

Final Office Action issued in U.S. Appl. No. 10/037,266, dated Mar. 9, 2004.

PCT International Search Report and Written Opinion, in Application PCT/US2011/026763, dated Nov. 14, 2011.

PCT Written Opinion, in Application PCT/US2011/026741, dated Nov. 28, 2011.

Applicants' Reply to Written Opinion, filed Feb. 28, 2012, in App. PCT/US2011/026741.

Cross-reference is made to U.S. Appl. No. 13/243,980, filed on Sep. 23, 2011.

Cross-reference is made to PCT Application No. PCT/US11/53120, filed on Sep. 23, 2011.

Cross-reference is made to U.S. Appl. No. 13/326,196, filed on Dec. 14, 2011.

Cross-reference is made to PCT Application No. PCT/US11/64989, filed on Dec. 14, 2011.

Cross-reference is made to U.S. Appl. No. 13/171,400, filed Jun. 28, 2011.

Cross-reference is made to U.S. Appl. No. 13/367,252, filed Feb. 6, 2012.

* cited by examiner

TISSUE LEAFLET ASSEMBLY ATTACHED WITHIN FRAME TO FORM A PROSTHETIC HEART VALVE (PLEATS NOT SHOWN, SEE FIG. 8L)

POSSIBLE SUTURE POINTS
864

860

Stress-strain curves in wet or hydrated state of five samples. Each curve corresponds to a separate sample.

Tissue Leaflet Assembly Attached in Frame
to Form Implantable Prosthetic Heart Valve Surgeon Holding a Premounted Percutaneously Deliverable
Heart Valve Associated With a Catheter and Residing Within
Sterile Packaging

PERCUTANEOUSLY DELIVERABLE HEART VALVE AND METHODS ASSOCIATED THEREWITH

CROSS-REFERENCE TO RELATED APPLICATIONS

The present application claims the benefit of U.S. Provisional Patent Application No. 61/309,109 filed on Mar. 1, 2010, the content of which is incorporated herein by reference in its entirety. Cross-reference is made to U.S. patent application Ser. No. 13/038,260 filed on Mar. 1, 2011, the content of which is incorporated herein by reference. Cross-reference is also made to U.S. patent application Ser. No. 10/887,688 filed on Jul. 10, 2004, which is a continuation-in-part application of U.S. patent application Ser. No. 10/037,266 filed on Jan. 4, 2002.

FIELD

The present invention relates to the field of medical devices, and more particularly, to a percutaneously deliverable heart valve and a method of making a percutaneously deliverable heart valve.

BACKGROUND

Heart valve disease is a common degenerative condition that compromises physiologic function and causes limiting symptoms and threat to life in millions of patients all over the world. There are various underlying causes, but malfunction of heart valves is ultimately expressed as insufficient conduction of blood through the plane of the valve due to narrowing of the anatomic pathway (stenosis), or as incompetent closure that allows blood to return back through the valve again, thereby reducing the effective forward conduction of blood through the valve (insufficiency or regurgitation). These hemodynamic states lead to 1) deficiency of cardiac output and 2) adverse loads on the pumping chambers of the heart, both of which in turn lead to functional compromise of the patient and often premature death unless effectively corrected.

Definitive corrective treatment of heart valve disease is conventionally performed by open-chest surgical techniques, wherein the valve is manipulated, repaired, or replaced with a prosthetic valve under direct vision. Heart valve surgery is performed in hundreds of thousands of cases yearly worldwide, but carries a high burden of cost, morbidity, and mortality, especially in susceptible patients who may be elderly or otherwise physiologically compromised by collateral disease. Further, the costs and resource requirements of the surgical enterprise restrict the availability of heart valve replacement to many more patients all over the world.

In pursuit of alternatives to heart valve surgery, over the last ten years a number of development programs have brought percutaneous, trans-catheter implantation of prosthetic heart valves into commercial use in the European Union (EU) and into pivotal clinical trials in the United States of America. Initial clinical experience in the EU was directed toward patients who had critical aortic valve stenosis, but were deemed to be at unacceptably high risk for open-heart surgical valve replacement. In several thousand such cases, utilizing both balloon-expandable and self-expanding designs in two separate programs, percutaneous heart valve replacement (PHVR) was shown to be feasible and possibly competitive with surgery in selected patients with 12-18 month mortality rates of about 25%. Grube E., et al., *Progress and Current Status of Percutaneous Aortic Valve Replacement: Results of Three Device Generations of the CoreValve Revalving System*, Circ. Cardiovasc Intervent. 2008; 1:167-175.

The application of PHVR thus far has been challenged by the technical difficulties of the implantation sequence—especially in the aortic valve position. The technique for available devices is limited by the large caliber of the devices and their delivery catheters; often, if it can be done at all in some smaller arteries, open surgical exposure and management of the femoral artery is required to insert the 18-24 French (6-8 mm diameter) systems, and their bulkiness inside the central arteries can threaten the safety of the delivery sequence. Further, access site bleeding complications form a significant part of the adverse events of the procedures.

Typically, the current PHV designs comprise a biological membrane forming the operating leaflets of the valve, attached within a metal frame, that is then collapsed onto a delivery catheter or balloon, and then constrained within an outer sheath. After an initial dilation of the diseased valve with a large balloon, this assembly is then advanced to the plane of the valve and deployed by self-expansion or by balloon expansion.

The effective caliber of the valve delivery system is determined by the total bulk of each coaxially mounted component. The bulk of the PHV itself is determined by the diameter of the frame and by the thickness, stiffness, and particular arrangement of the inner membrane forming the operating leaflets of the valve. The characteristic thickness of current PHV membranes is thus a limiting factor in the ultimate delivery profile of the PHV. Such characteristic membrane thickness is, in turn, a result of the methods by which it is processed and ultimately delivered for use. Typically, glutaraldehyde fixation (for protein cross-linking) of animal tissue is employed to produce suitable biological membranes for incorporation. Requirements for strength and durability have determined the most useful ranges for tissue thickness and cross-linking while typically imposing countervailing stiffness and brittleness. Subsequent hydration in suitable solutions improves these characteristics, but the hydrated membrane by this means also gains thickness.

One of the evident requirements for a PHV design is that the valve functions with a high degree of competence immediately on deployment, since the patient's hemodynamic survival depends on it. To this end, in part, like surgical valve prostheses, current PHV designs are completed, transported, and delivered for use in a hydrated state in a jar of solution. In use, commercially available surgical and percutaneously implanted bioprosthetic heart valves are rinsed and prepared before use in a "wet" state. More particularly, commercially available prosthetic heart valves are rinsed, crimped, and mounted in the catheterization lab. Accordingly, problems with current commercially available prosthetic heart valves include the time, cost and variability associated with the necessity to rinse, crimp, and mount the valve in the catheterization lab. That is, current mounting of prosthetic heart valves in the catheterization lab imposes one or more of delay, cost, technical burdens and possible errors. Avoiding one or more of these problems would be advantageous. In addition, current "wet" valve designs impose additional profile on the collapsed valve. The hydrated membrane, while having desirable and necessary flexibility for reliable operation immediately on deployment, also imposes a large part of the thickness of the assembled and mounted valve that compromises its deliverability.

Expanding on some of the problems described above, the use of current PHVs in the catheter lab requires a number of preparatory acts that are potentially troublesome and can prolong the delivery sequence during a critical phase of the procedure. Since PHVs are delivered for use "wet" in a preservative solution, they have to be treated prior to insertion with a series of cleansing and hydrating solutions. Once this is completed, the PHVs have to be mounted on their delivery catheters. Special crimping and mounting tools are needed in the case of the balloon-expandable Edwards Sapien valve, for example. Accordingly, there is a need to address the shortcomings discussed above.

SUMMARY

It is to be understood that the present invention includes a variety of different versions or embodiments, and this Summary is not meant to be limiting or all-inclusive. This Summary provides some general descriptions of some of the embodiments, but may also include some more specific descriptions of other embodiments.

In at least one embodiment, a substantially "dry" membrane PHV system is provided wherein a tissue material is prepared and folded in a dry state to form a tissue leaflet assembly. Thereafter, the tissue leaflet assembly is attached to a frame to form an implantable prosthetic heart valve that is subsequently pre-mounted in an integrated catheter delivery system. The catheter delivery system that includes the prosthetic heart valve is then packaged and transported while the tissue leaflet assembly remains substantially dry. The prosthetic heart valve is available for use directly out of its package envelope. Accordingly, it can be inserted into the body without need of hydration, crimping or mounting tools, or other preparatory acts. That is, the tissue forming the tissue leaflet assembly of the prosthetic heart valve can be treated and dried, then while remaining dry, folded into a tissue leaflet assembly. Thereafter, the tissue leaflet assembly is at least partially rehydrated and then attached within a frame, such as a stent, to form an implantable prosthetic heart valve. The tissue leaflet assembly of the prosthetic heart valve is then allowed to dry. The prosthetic heart valve can thereafter be subsequently packaged, delivered, and shipped while the tissue leaflet assembly of the prosthetic heart valve remains in a dry condition. The prosthetic heart valve can then be implanted into the receiving patient. Accordingly, the PHV system simplifies arterial insertion, and, as the dry condition also confers lower bulk and profile, procedural manipulation and associated complications may be reduced if not eliminated. In addition, one or more embodiments of the present invention widen the candidacy of patients with smaller arteries for the PHV procedure. As an added advantage, at least one embodiment of the present invention allows the implantation to take place under shorten elapsed times at the most critical phase of the procedure.

In at least one embodiment, a membrane PHV system is provided wherein a tissue material is prepared and folded in a dry state to form a tissue leaflet assembly, and further wherein the tissue leaflet assembly is thereafter at least partially hydrated and attached to a frame that is subsequently pre-mounted in an integrated catheter delivery system.

In at least one embodiment, a membrane PHV system is provided wherein a tissue material is prepared and folded in a dry state to form a tissue leaflet assembly, and further wherein the tissue leaflet assembly is at least partially hydrated and attached to a frame to form the prosthetic heart valve. Thereafter, the prosthetic heart valve is allowed to dry and subsequently pre-mounted in an integrated catheter delivery system after which the tissue leaflet assembly of the prosthetic heart valve remains dry, and wherein the system is then associated with a package for shipment while the tissue leaflet assembly remains dry.

In at least one embodiment, a membrane PHV system is provided wherein a tissue material is prepared and then folded in a dry state to form a tissue leaflet assembly, and further wherein the tissue leaflet assembly is at least partially hydrated and attached to a frame to form the prosthetic heart valve. Thereafter, the prosthetic heart valve is allowed to dry and subsequently pre-mounted in an integrated catheter delivery system after which the tissue leaflet assembly of the prosthetic heart valve is then at least partially hydrated and associated with a package for shipment.

In at least one embodiment, an article adapted for transcatheter delivery into a patient is provided, comprising: a prosthetic heart valve further comprising a treated tissue attached to a frame, wherein the treated tissue comprises a thickness of about 50 to 500 micrometers and an ultimate tensile strength of greater than about 15 MegaPascals when at a water content of less than about 50% by weight of the section of treated tissue. Here it is noted that the tensile strength of the treated tissue described herein is higher than the tensile strength of other known prepared tissues, whether hydrated or dry. In at least one embodiment, the water content of the treated tissue is less than about 40% by weight of the treated tissue. In at least one embodiment, the ultimate tensile strength is greater than about 20 MegaPascals. In at least one embodiment, the treated tissue does not include a matrix that has been exposed to a polymer infiltrate. In at least one embodiment the treated tissue comprises a treated pericardium tissue.

In at least one embodiment, the method further comprises exposing the section of tissue to light energy for an exposure duration, the exposure duration extending until there is no further visible separation of lipid droplets from an exposed surface of the section of tissue. In at least one embodiment, the light energy is at least equivalent to exposing the section of tissue to a 25-100 watt light source, and more preferably, a 50 watt incandescent light source with a flat radiant face situated at a distance of about 10 centimeters from the exposed surface for about 15 minutes. In at least one embodiment, the method further comprises: (d) rinsing the section of tissue with distilled water and isopropyl alcohol for a post-fixation period of time of not less than about 7 days; wherein step (d) occurs after step (c).

In at least one embodiment, an article adapted for implantation in a patient is provided, comprising: a prosthetic heart valve further comprising a treated tissue attached to a frame, wherein the treated tissue comprises a water content of less than about 60% by weight of the treated tissue. In at least one embodiment, the treated tissue comprises a section of pericardium tissue having an ultimate tensile strength of greater than about 12 MegaPascals. In at least one embodiment, the section of treated tissue comprises a thickness of between about 50 to 300 micrometers. In at least one embodiment, the water content of the treated tissue is less than about 40% by weight of the treated tissue.

As used herein, the term "dry" (or "substantially dry") when referring to the state of the tissue that forms the heart valve of the percutaneous heart valve means a moisture content less than the water moisture content of the tissue when the tissue is allowed to fully rehydrate in the body of a patient. Typically, pericardium tissue treated in accordance with one or more embodiments described herein is about 70% by weight water when fully hydrated. Drying to a constitution of less than 40% by weight of water usefully alters the handling properties for purposes of folding and sewing the tissue. As those skilled in the art will appreciate, the moisture content of the tissue may vary when dry. For example, the moisture content of the tissue when being folded and dry may be different than the moisture content of the tissue when dry and being shipped in a premounted state within a catheter delivery system.

Advantageously, at least one embodiment of the one or more present inventions is directed to a prosthetic heart valve that is mounted onto a valve delivery system and stored in a sterile package. Accordingly, in at least one embodiment, an assembly is provided, comprising:

a prosthetic heart valve including:
a frame; and
a tissue leaflet assembly attached to the frame;
a percutaneously insertable valve delivery mechanism, wherein the prosthetic heart valve is releasably mounted onto the percutaneously insertable valve delivery mechanism; and
sterile packaging containing the prosthetic heart valve releasably mounted onto the percutaneously insertable valve delivery mechanism.

In at least one embodiment, the percutaneously insertable valve delivery mechanism comprises a balloon catheter. In at least one embodiment, the balloon catheter is a 12 to 14 French balloon catheter. In at least one embodiment, the balloon catheter is less than about 12 French. In at least one embodiment, the balloon catheter is between about 5 to 12 French. In at least one embodiment, the percutaneously insertable valve delivery mechanism comprises a mandrel. In at least one embodiment, tissue forming the tissue leaflet assembly within the sterile packaging is at least one of hydrated and not substantially dry. In at least one embodiment, tissue forming the tissue leaflet assembly within the sterile packaging is substantially dry. In at least one embodiment, the frame comprises a stent. In at least one embodiment, tissue forming the tissue leaflet assembly comprises treated pericardium tissue.

At least one embodiment of the one or more present inventions includes a prosthetic heart valve for implantation in a patient. Accordingly, a pre-packaged percutaneous, trans-catheter deliverable prosthetic heart valve ready for implantation in a patient is provided, comprising:

a frame; and,
a tissue leaflet assembly attached to the frame, the tissue leaflet assembly comprising a substantially dry tissue.

In at least one embodiment, the substantially dry tissue comprises treated pericardium tissue. In at least one embodiment, the frame and tissue leaflet assembly attached thereto are operably associated with a 12 to 14 French balloon catheter. In at least one embodiment, the frame and tissue leaflet assembly attached thereto are operably associated with a balloon catheter having a size of less than about 12 French. In at least one embodiment, the frame and tissue leaflet assembly attached thereto are operably associated with a balloon catheter having a size of between about 5 to 12 French. In at least one embodiment, the substantially dry tissue comprises a water moisture content of less than about 40% by weight of the substantially dry tissue.

In at least another embodiment, an assembly for use with a patient is provided, comprising:

a sealed sterile package containing a delivery system for percutaneously deploying a heart valve in the patient, the heart valve including:
a frame releasably mounted on the delivery system within the sealed sterile package; and
a tissue leaflet assembly attached to the frame.

In at least one embodiment, the tissue leaflet assembly comprises pericardium tissue.

In at least one embodiment, a method is provided, comprising:

partially compressing and mounting a prosthetic heart valve upon a delivery catheter, the prosthetic heart valve comprising a tissue;
allowing the tissue to at least partially dry;
further compressing and mounting the prosthetic heart valve upon the delivery catheter; and
sterilizing and packaging the prosthetic heart valve and delivery catheter.

In at least one embodiment, the method further comprises transporting the sterilized and packaged prosthetic heart valve and delivery catheter. In at least one embodiment, the tissue comprises treated pericardium tissue. In at least one embodiment, prior to partially compressing and mounting the prosthetic heart valve upon the delivery catheter, the tissue is at least one of (a) not substantially dry, and (b) at least partially hydrated.

For the various embodiments described herein, the prosthetic heart valve, including the tissue leaflet assembly, comprises membrane tissue other than pericardium tissue.

In at least one embodiment, a method is provided, comprising:

attaching pericardium tissue to a frame;
partially compressing and mounting the frame, with the tissue attached thereto, upon a delivery catheter;
allowing the tissue to at least partially dry;
further compressing and mounting the frame, with the tissue attached thereto, upon the delivery catheter; and
sterilizing and packaging the frame and delivery catheter, with the tissue attached thereto.

In at least one embodiment, prior to partially compressing and mounting the frame, the tissue is at least one of (a) not substantially dry, and (b) at least partially hydrated. In at least one embodiment, the method further comprises transporting the sterilized and packaged frame, with the tissue attached thereto, mounted upon the delivery catheter, to a surgical or medical procedure facility. In at least one embodiment, prior to attaching the tissue to the frame the tissue is folded to form a tissue leaflet assembly. In at least one embodiment, the tissue leaflet assembly comprises at least one cuff and at least one pleat.

In at least one embodiment, a method of preparing a percutaneous, trans-catheter prosthetic heart valve is provided, the method comprising:

providing a membrane tissue from an organism;
treating the membrane tissue with at least one chemical to produce a treated membrane tissue;
drying the treated membrane tissue until it is a substantially dry tissue;
attaching the substantially dry tissue in a frame;
rehydrating the substantially dry tissue that is attached within the frame to form a rehydrated tissue;
collapsing the frame with the rehydrated tissue attached thereto; and
drying the rehydrated tissue within the collapsed frame until it is a substantially dry tissue.

In at least one embodiment the method further comprises compressing and mounting the frame, with the substantially dry tissue attached thereto, upon a delivery catheter. In at least one embodiment the method further comprises sterilizing and packaging the frame, with the substantially dry tissue attached thereto, mounted upon the delivery catheter. In at least one embodiment, the treating comprises sterilizing the frame with the substantially dry tissue attached thereto with exposure to at least one of ethylene oxide, a proton beam, and gamma radiation. In at least one embodiment, the method further comprises shipping the sterilized and packaged frame with the substantially dry tissue attached thereto, mounted upon the delivery catheter, to a surgery or medical procedure facility. In at least one embodiment, prior to the attaching step the dry tissue is not folded to provide a cuff and/or a pleat. In at least one embodiment, prior to the attaching step the dry tissue is folded to form a tissue leaflet assembly. In at least one embodiment, the tissue leaflet assembly comprises at least one cuff and at least one pleat.

In at least one embodiment, the method of preparing a percutaneous, trans-catheter prosthetic heart valve further comprises implanting the frame with the substantially dry tissue attached thereto into a patient. In at least one embodiment, the frame comprises a stent. In at least one embodiment, the method further comprises mounting the frame and the tissue leaflet assembly attached thereto upon a 12 to 14 French balloon catheter. In at least one embodiment, the method further comprises mounting the frame and the tissue leaflet assembly attached thereto upon a balloon catheter having a size of less than about 12 French. In at least one embodiment, the method further comprises mounting the frame and the tissue leaflet assembly attached thereto upon a balloon catheter having a size of between about 5 to 12 French. In at least one embodiment, the method further comprises mounting the frame and the tissue leaflet assembly attached thereto on a mandrel. In at least one embodiment, the method of preparing a percutaneous, trans-catheter prosthetic heart valve further comprises immersion of the membrane tissue in buffered or unbuffered 1-37.5% formalin for between about 3 days to 3 weeks. In at least one embodiment, the method of preparing a percutaneous, trans-catheter prosthetic heart valve further comprises immersion of the membrane tissue in buffered or unbuffered 1-37.5% formalin for between about 3 days to 5 weeks. In at least one embodiment the treating comprises immersion of the membrane tissue in 100% glycerol for greater than 3 weeks. In at least one embodiment the treating comprises immersion of the membrane tissue in 0.1-25% glutaraldehyde for between about 3 days to 3 weeks. In at least one embodiment the treating comprises immersion of the membrane tissue in 0.1-25% glutaraldehyde for between about 3 days to 5 weeks. In at least one embodiment the treating comprises immersion of the membrane tissue in oligomeric filtered 0.1-25% glutaraldehyde for between about 3 days to 3 weeks. In at least one embodiment the treating comprises immersion of the membrane tissue in oligomeric filtered 0.1-25% glutaraldehyde for between about 3 days to 5 weeks. In at least one embodiment the treating comprises immersion of the membrane tissue in the aforementioned formalin, glutaraldehyde, or oligomeric filtered glutaraldehyde solutions with the added free amino acids lysine and/or histidine. In at least one embodiment the treating does not include contact and/or exposure to a polymer to infiltrate and/or encapsulate tissue fibers of the tissue.

In at least one embodiment, a method of preparing a percutaneous, trans-catheter prosthetic heart valve is provided, the method comprising:

providing a section of tissue harvested from a mammalian organism; and causing osmotic shocking of the section of tissue by performing multiple rinses of the section of tissue with distilled water. In at least one embodiment, the method further comprises hydrating the section of tissue during a plurality of time intervals using distilled water. In at least one embodiment the section tissue comprises pericardium tissue. In at least one embodiment, the method further comprises not using saline for causing at least one of the osmotic shocking and the hydrating of the tissue. In at least one embodiment, the method further comprises pretreating the section of tissue with glycerol before contacting the section of tissue with one or more of isopropyl alcohol, glutaraldehyde and formalin. In at least one embodiment, the method further comprises contacting the section of tissue with a solution containing formalin after pretreating the section of tissue with glycerol. In at least one embodiment, the method further comprises contacting the section of tissue with a solution containing glutaraldehyde after pretreating the section of tissue with glycerol. In at least one embodiment, the method further comprises pretreating the section of tissue with isopropyl alcohol before contacting the section of tissue with either glutaraldehyde and formalin. In at least one embodiment, the method further comprises contacting the section of tissue with a solution containing formalin after pretreating the section of tissue with isopropyl alcohol. In at least one embodiment, the method further comprises contacting the section of tissue with a solution containing glutaraldehyde after pretreating the section of tissue with isopropyl alcohol. In at least one embodiment, the method further comprises exposing the section of tissue to light energy for a period time, the period of time extending until there is no further visible separation of lipid droplets from an exposed surface of the section of tissue. In at least one embodiment, the light energy is at least equivalent to exposing the section of tissue to a 50 watt incandescent light source with a flat radiant face situated at a distance of about 10 centimeters from the exposed surface for about 15 minutes.

With regard to delivery characteristics, another significant advantage of an implantable prosthetic heart valve using a relatively thin tissue component described herein is that the implantable prosthetic heart valve offers a relatively low packing volume as compared to commercially available prosthetic heart valves. As a result, the implantable prosthetic heart valve provides a relatively low catheter delivery profile, thereby enabling implantation in patients possessing relatively small diameter vascular systems.

In accordance with one or more embodiments, a dry tissue membrane has substantially less mass than a wet membrane. By way of example, a substantially dry pericardium tissue prepared by one or more of the present embodiments has approximately 30% of the mass of a wet pericardium tissue, and marked reduction in profile and packing volume, thereby achieving a relatively low profile and making it suitable for implantation in greater number of patients, especially those having small diameter vascular systems. In addition, a dry prosthetic heart valve does not require storage and transport in preservative. A dry prosthetic heart valve can be mounted on a delivery catheter at its location of manufacture, which allows for pre-packaging of an integrated delivery system. Together with a relatively low profile, embodiments of the prosthetic heart valves thereby offer reliability and convenience because the implantable prosthetic heart valve is pre-mounted upon a delivery catheter and forms part of a pre-packaged delivery system. In addition, a dry prosthetic heart valve does not require rinsing, rehydration, or mounting upon a delivery catheter in a catheterization lab. Therefore, a dry prosthetic heart valve can be inserted directly from package into the body at a critical time during the procedure. Advantageously, this avoids procedure time, manipulation, and errors of mounting, crimping, and orienting catheters and sheaths. Once at the surgical facility/location, the dry prosthetic heart valve is inserted and delivered by balloon catheter expansion in the plane of the diseased valve in the standard way and the dry prosthetic heart valve begins to function immediately, even in its dry state or not fully rehydrated state (because some rehydration will occur upon flushing of the catheter with the prosthetic heart valve residing therein), with rehydration of the tissue membrane subsequently completing naturally in the body.

Various components are referred to herein as "operably associated." As used herein, "operably associated" refers to components that are linked together in operable fashion, and encompasses embodiments in which components are linked directly, as well as embodiments in which additional components are placed between the two linked components.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

As used herein, "sometime" means at some indefinite or indeterminate point of time. So for example, as used herein, "sometime after" means following, whether immediately following or at some indefinite or indeterminate point of time following the prior act.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

To further clarify the above and other advantages and features of the one or more present inventions, a more particular description of the one or more present inventions is rendered by reference to specific embodiments thereof which are illustrated in the appended drawings. It is appreciated that these drawings depict only typical embodiments of the one or more present inventions and are therefore not to be considered limiting of its scope. The one or more present inventions is described and explained with additional specificity and detail through the use of the accompanying drawings in which.

The drawings are not necessarily to scale.

DETAILED DESCRIPTION

Embodiments of the one or more inventions described herein include one or more devices, assemblies and/or methods related to a prosthetic heart valve. A prosthetic heart valve in accordance with at least one embodiment described herein can be surgically implanted, such as by percutaneous, transcatheter delivery, to the implantation site within the patient. One or more embodiments of the prosthetic heart valves described herein have application for at least aortic and pulmonary valve positions, including for structural defects and diseased valves.

In at least one embodiment, biocompatible material is attached within a frame to form an implantable prosthetic heart valve, and then at a later time, the implantable prosthetic heart valve is implanted within a patient, such as by way of a percutaneous, trans-catheter delivery mechanism. Once implanted, the prosthetic heart valve serves to regulate the flow of blood associated with the patient's heart by allowing forward blood flow and substantially preventing backflow or valvular regurgitation.

Figure 1:
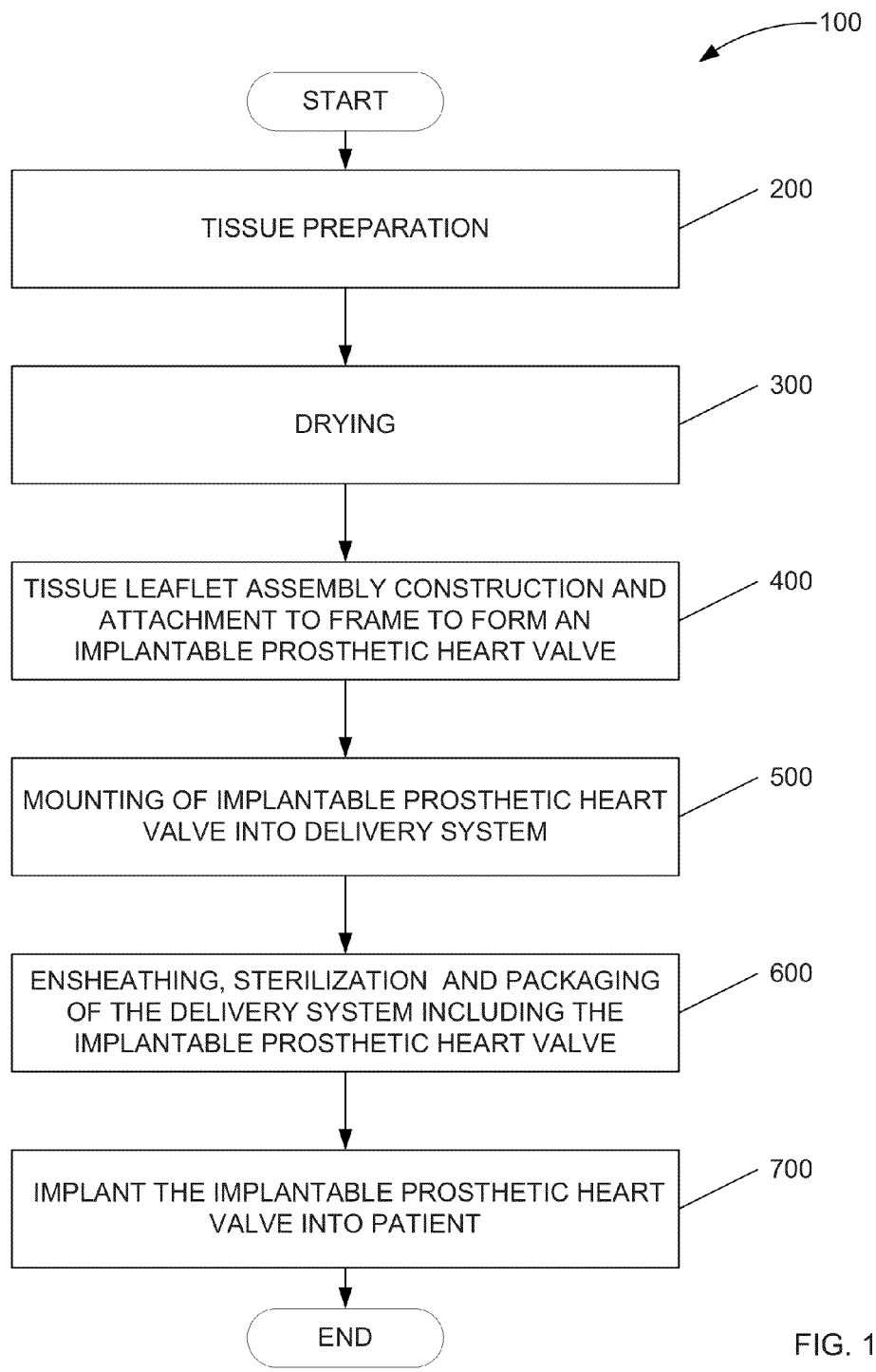
FIG. 1 is a flow chart of a method associated with at least of one embodiment of the present invention.

Referring now to FIG. 1, a flow chart illustrates at least one embodiment of a prosthetic heart valve preparation and delivery method 100. The prosthetic heart valve preparation and delivery method 100 generally includes a plurality of procedures to include tissue preparation at 200, drying at 300, tissue leaflet assembly construction and attachment to frame at 400 to form an implantable prosthetic heart valve, mounting of the prosthetic heart valve (that is, the frame with the tissue leaflet assembly) into a delivery system at 500, ensheathing, sterilizing and packaging the delivery system including the prosthetic heart valve at 600, and finally, delivering the prosthetic heart valve into the patient at 700. Further detail of the prosthetic heart valve preparation and delivery method 100 is provided below.

At least one or more embodiments described herein include a relatively thin tissue component. By way of example and not limitation, in at least one embodiment the tissue has a thickness of approximately 50-150 µm, and further possesses characteristics of pliability and resistance to calcification after implantation. The relatively thin nature of the tissue used in the implantable prosthetic heart valve assists with biocompatibility. In addition, the relatively thin tissue component thereby provides for a relatively low mass. As a result, an implantable prosthetic heart valve using the tissue can accelerate to a relatively high heart rate in beats per minute with competent function.

Tissue suitable for use in the one or more prosthetic heart valves and/or one or more assemblies described herein is relatively thin and can generally be considered to be a membrane. Those skilled in the art will appreciate that both natural and synthetic types of materials may be used to form a leaflet assembly of a prosthetic heart valves. Accordingly, it is to be understood that although treated pericardium tissue is described as a suitable material for use in the leaflet assembly of a prosthetic heart valve of one or more embodiments described herein, material other than xenograft tissue membrane can be used, and indeed, xenograft tissue membrane other than pericardium tissue can be used. More specifically, synthetic materials may include, but are not limited to, PTFE, PET, Dacron, and nylon. In addition, other than pericardium tissue, xenograft tissue membrane may include, but is not limited to, membrane material from the intestine, lung and brain. Suitable material may also comprise allograft material, that is, material from human sources. The listing of possible materials is for exemplary purposes and shall not be considered limiting.

Figure 2A:
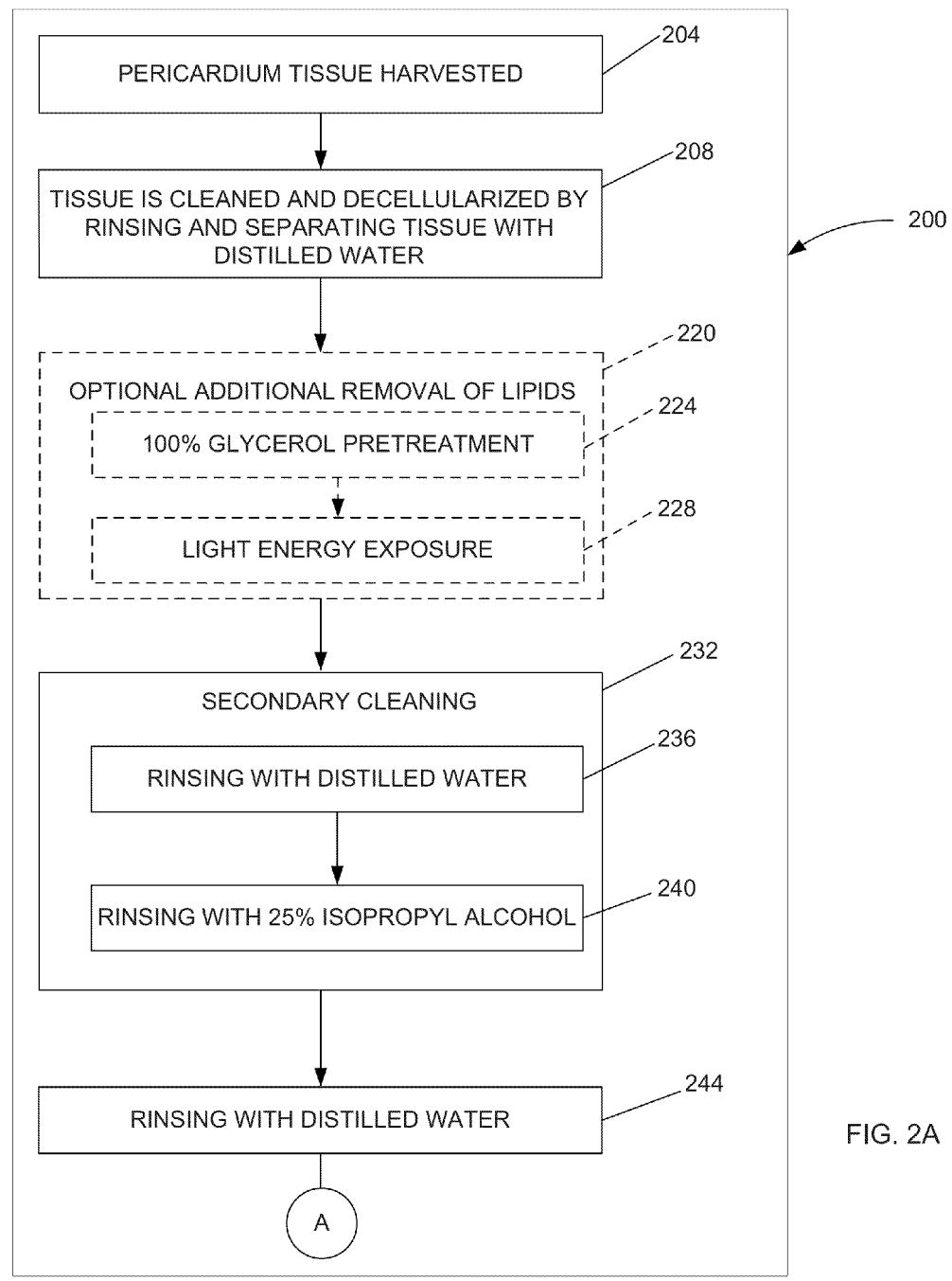
FIGS. 2A-2B are a flow chart illustrating elements of the tissue preparation.

With reference now to FIG. 2A, the process associated with preparation of a biocompatible tissue consistent with the above-noted characteristics is described. In at least one embodiment, pericardium tissue, such as porcine or bovine pericardium tissue, is harvested at 204 and then processed to serve as the biocompatible tissue for association with a frame, such as by attaching within a frame. Accordingly, subsequent to the harvesting at 204, the pericardium tissue is cleaned and decellularized at 208. More particularly, in at least one embodiment the tissue is initially cleaned with distilled water using gentle rubbing and hydrodynamic pressure at 208 in order to remove adherent non-pericardial and non-collagenous tissue. In at least one embodiment, the hydrodynamic pressure at 208 is provided by spraying the tissue with a relatively weak stream of liquid to remove at least some of the non-collagenous material associated with the tissue. The rinsing at 208 is to achieve effective decellularization of the pericardium tissue through osmotic shock. Typically, the thickness of the tissue in the cleaned condition varies from about 50 to 500 micrometers, depending on the source of raw tissue. Cleaning preferably continues until there is no visible adherent non-pericardial or non-collagenous tissue.

With continued reference to FIG. 2A, after the tissue has been cleaned and decellularized at 208, the tissue then undergoes optional additional removal of lipids at 220 to further treat the tissue for preventing immunologic response and calcification. More particularly, the tissue first optionally undergoes a 100% glycerol pretreatment at 224 while being positioned on a flat surface (e.g., an acrylic plate), after which the tissue becomes nearly transparent.

At 228, the tissue optionally undergoes a "thermophotonic" process. In at least one embodiment, the tissue is optionally exposed to light energy for additional removal of lipids and for initial cross-linking of the collagen. By way of example and not limitation, in at least one embodiment a 25-100 watt incandescent light source, and more preferably, a 50 watt incandescent light source with a flat radiant face is employed at a distance of about 10 centimeters from the tissue surface, typically requiring 15 minutes of exposure before further visible separation of lipid droplets from the tissue stops.

Still referring to FIG. 2A, the tissue is then cleaned again in secondary cleaning at 232. More particularly, at 236 the tissue is again rinsed with distilled water. Thereafter, at 240 the tissue is rinsed with 25% isopropyl alcohol for periods of several hours to several days and weeks, depending on the desired tissue properties of pliability and tensile strength. By way of example and not limitation, tissue has been successfully prepared by rinsing with 25% isopropyl alcohol for a period of 7 days, and after further treatment steps described herein, provided an ultimate tensile strength of greater than 25 MegaPascals. Here, the combination of tissue pliability and tensile strength is sought for purposes of producing a material having property characteristics suitable for being physically manipulated to form a tissue leaflet assembly or other configuration appropriate for attaching with a frame, while providing a tissue material that will operate properly once implanted. These techniques are intended to conserve and preserve collagen fibers, minimizing damage to the tissue and improving tissue characteristics. The preparation and fixation techniques produce tissue membrane material that may be rendered and used at lesser thickness than typically rendered in the prior art. Thinner membranes are more pliable, but with conventional preparation techniques the tensile strength of the tissue is sacrificed. Advantageously, the preparation techniques described herein have produced membranes that have as much as three times the tensile strength of a commercial product of the prior art. This achieved strength is thus enabling for providing a tissue leaflet assembly having a low profile with appropriate durability, even in a substantially dry state. More particularly, the tissue possesses a relatively high tensile strength. By way of example and not limitation, testing has shown that embodiments of tissue prepared as described herein provide a tissue with a tensile strength of approximately three times the tensile strength of current pericardial valve tissue, such as on the order of approximately 25 MegaPascals, thereby providing about 2000 times the physiologic load strength for valve tissue. Moreover, testing of an embodiment of an implantable prosthetic heart valve made with tissue prepared as described herein and under a static load of greater than approximately 250 mmHg showed less than approximately 14% leakage, wherein such results are generally considered superior to surgical tissue valve prostheses.

In at least one embodiment where isopropyl alcohol is described as a rinsing agent, ethanol may be used in its place as an alternative, although resulting tissue properties may vary.

Figure 9:
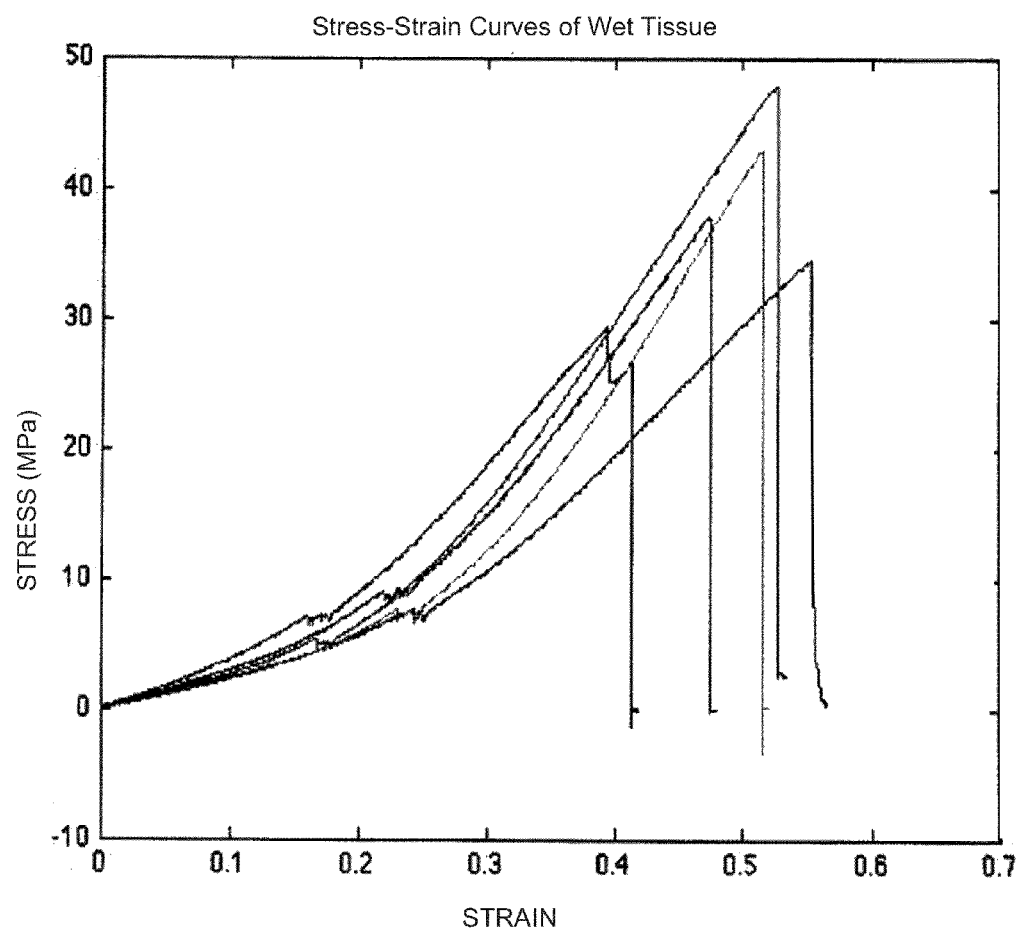
FIG. 9 is a graph that shows actual stress-strain test results for five tissue samples prepared in accordance with at least one embodiment.

With reference to FIG. 9, stress-strain curve results for five different tissue samples prepared in accordance with an embodiment are shown. For the testing results shown, the yield stress or ultimate tensile strength was obtained by mounting strips of tissue fixed at the ends in a linear force tester and increasing the length by 0.3 mm/sec while recording resultant force (tension) until the material ruptured or separated entirely; these measurements were then used to calculate the stress-strain curves depicted in FIG. 9. As illustrated in the graph, the yield stress or ultimate tensile strength of the various tissue samples varied from about 30 to about 50 MegaPascals. More particularly, for each curve shown in FIG. 9, the testing procedures were the same. That is, each of the curves shown pertain to separate pieces of tissue that were subjected to the same test. The results show a minimum ultimate tensile strength of 30 MegaPascals, with a range up to 50 MegaPascals. Accordingly, the illustrated test results demonstrate consistency of the ultimate tensile strength results for the tissue treatment process.

With reference back to FIG. 2A, the tissue is rinsed with distilled water at 244 as a final cleaning step and for rehydration.

Figure 2B:
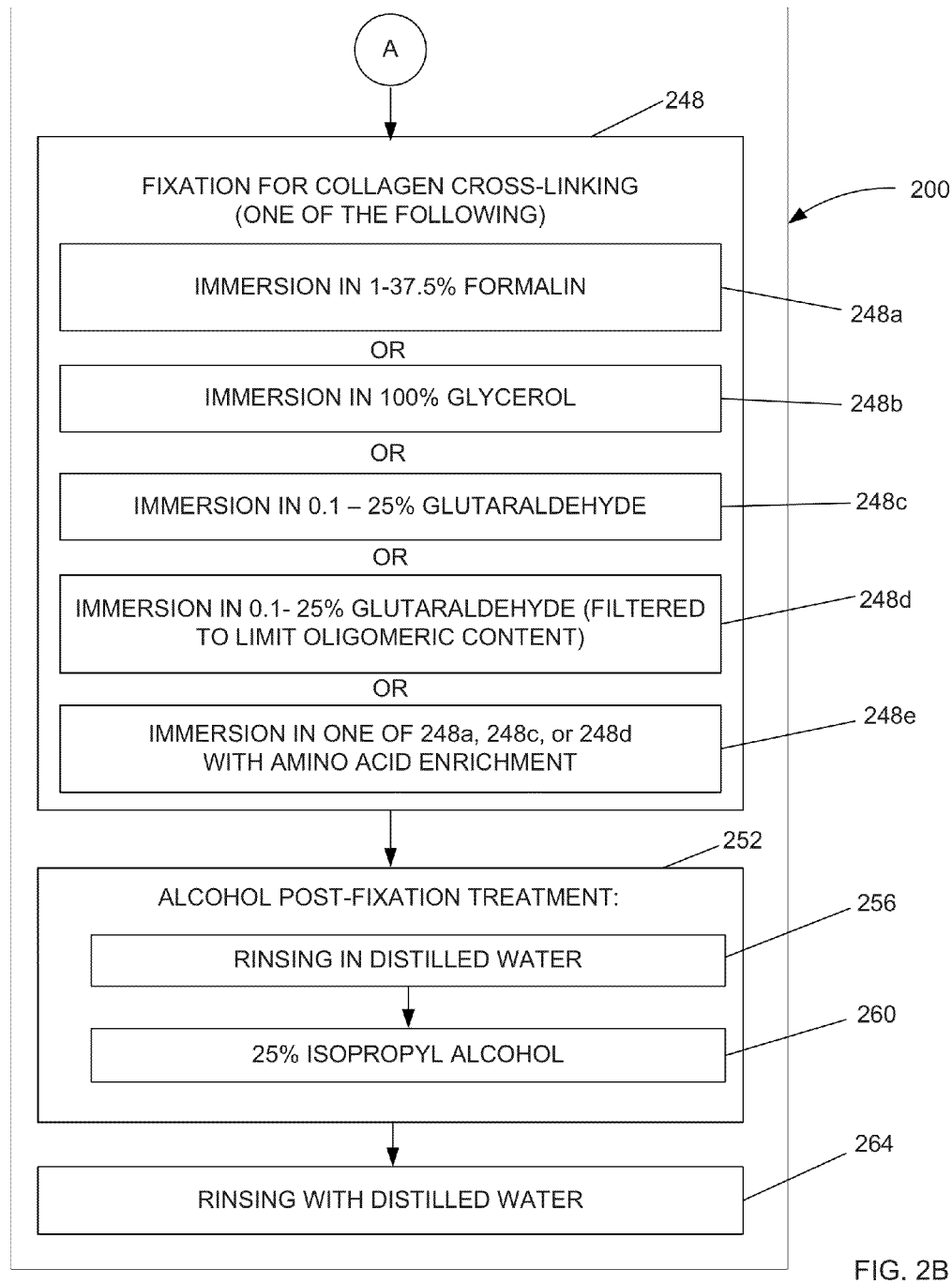

Referring now to FIG. 2B, following the rinse with distilled water at 244, treatment of the tissue continues. More particularly, fixation for collagen cross-linking at 248 is achieved by performing at least one of the following:

a. At 248a, immersion of the tissue in 1-37.5% formalin, ideally a buffered solution, for between about 3 days to 5 weeks, and more preferably, for between about 3 days to 4 weeks, and more preferably yet, for between about 3 weeks to 4 weeks, at a temperature of between about 4 to 37° C., and more preferably, 10% formalin for 6 days at 20° C.; or b. At 248b, immersion of the tissue in 100% glycerol for up to 6 weeks at between 4 to 37° C., and more preferably, immersion of the tissue in 100% glycerol for about 3 weeks at 20° C.; or c. At 248c, immersion of the tissue in 0.1-25% glutaraldehyde for between about 3 days to 5 weeks, and more preferably, for between about 3 days to 4 weeks, and more preferably yet, for between about 3 weeks to 4 weeks, at 0 to 37° C., and more preferably, immersion of the tissue in 0.25% glutaraldehyde for 7 days at 4° C.; or d. At 248d, immersion of the tissue in 0.1-25% glutaraldehyde (filtered to limit oligomeric content) for between about 3 days to 5 weeks, and more preferably, for between about 3 days to 4 weeks, and more preferably yet, for between about 3 weeks to 4 weeks, at 0 to 37° C., and more preferably, 0.25% glutaraldehyde for 7 days at 4° C.; or e. At 248e, immersion in the tissue in one of the above formalin, glutaraldehyde, or oligomeric filtered glutaraldehyde solutions together with added amino acids, lysine and/or histidine, wherein the concentration of the amino acids, L-lysine or histidine, used as an additive to the fixative is in the range of about 100-1000 milliMolar, with a preferred value of about 684 mM.

In addition to the foregoing, combinations of the processes listed above may be performed, including: step a followed by step b; step a followed by step c; and step a followed by step d.

As those skilled in the art will appreciate, heat-shrink testing may be conducted on tissue samples to correlate the effectiveness of protein cross-linking Here, results of heat-shrink testing performed on one or more samples of tissue prepared in accordance with at least one embodiment using formalin showed that the tissue had a shrink temperature of 90° C. This compares favorably with samples prepared using glutaraldehyde, wherein the shrink temperature was 80° C. Accordingly, formalin is a suitable variant of fixation. It is noted that formalin was generally abandoned by the field, largely because of material properties that were unfavorable and because of inadequate or unstable protein cross-linking. Such problems have been overcome through the pretreatments described herein, allowing production of tissue with strength, pliability, and durability in a relatively thin membrane. When used in a percutaneous deliverable heart valve (also referred to herein as "prosthetic heart valve"), the tissue characteristics imparted by the tissue preparation process facilitate formation of a construct having a relatively low-profile, which also thereby facilitates dry packaging of the prosthetic heart valve. The same advantages are also achieved using the pretreatments when using a glutaraldehyde process.

Referring still to FIG. 2B, after fixation for collagen cross-linking at 248, an alcohol post-fixation treatment at 252 is preferably performed by rinsing the tissue in distilled water at 256, and then at 260 rinsing the tissue in 25% isopropyl alcohol for between about 30 minutes to 14 days or more at between about 0 to 37° C., and more preferably, for at least about 7 days at 20° C. At 264, the tissue undergoes a rinsing with distilled water.

In accordance with at least one embodiment, treatment of the tissue, including from the time of harvest to the time of implantation or grafting, does not include contact and/or exposure to a polymer to infiltrate and/or encapsulate tissue fibers of the tissue.

Figure 3:
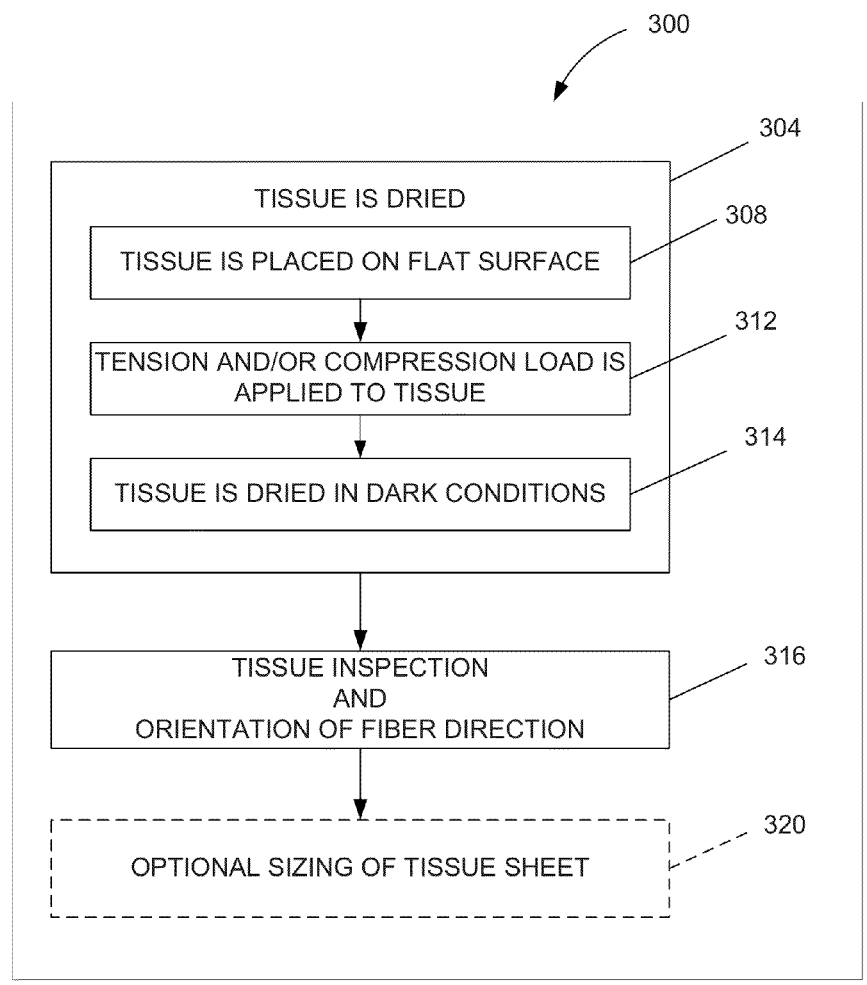
FIG. 3 is a flow chart illustrating elements of the drying and sizing.

Referring now to FIGS. 1 and 3, the drying process at 300 is performed after the tissue preparation at 200. Thus, in accordance with at least one embodiment, the tissue is dried under a load. More particularly, for the tissue drying at 304, the tissue is placed minimally stretched flat (that is, stretched just enough to eliminate visible wrinkles and bubbles) on a flat surface (e.g., a polymer or acrylic sheet) at 308, and held fixed at its edges at 312. Optionally, the joined tissue and underlying sheet are then set in a slight curve. The tension maintains the substantially flat structure of the tissue as it dries, thereby mitigating or preventing excessive shrinkage, wrinkling, and/or curling at the edges, and also making the rate of drying more uniform across the surface of the tissue because of the surface tension between the plate and the tissue. Alternatively, the tissue is dried while compressed between acrylic plates. When drying the tissue, the temperature is held at between about 4 to 37° C., and more preferably, between about 20 to 37° C. (i.e., approximately room temperature to normal human body temperature), and more preferably, at about 20° C. At 314, the drying process is performed in substantially dark conditions (i.e., substantially no visible light) for between about 6 hours to 5 days, and more preferably, for about 72 hours. By way of example, the tissue is dried in dark conditions at a temperature of about 20° C. for between about 6 hours to 5 days, and more preferably, for about 72 hours. As those skilled in the art will appreciate, drying the tissue while the tissue is compressed between plates requires a longer period of time.

In at least one embodiment, after drying, the tissue lots are inspected at 316, such as by stereomicroscopy, to identify and discard those with defects or discontinuities of the fiber matrix. In addition, the preferential fiber direction for each piece is identified to determine the necessary orientation of the free edge of the pieces that will form the valve leaflets. Depending upon the size (i.e., the area) of the tissue being prepared and the size of tissue needed for a given valve, the tissue may be trimmed or otherwise sized in optional sizing at 320, such as by cutting the tissue into an appropriately sized and shaped sheet for valve formation. Preferably, cutting of the tissue membrane is oriented so that the resulting free edge of the leaflet is parallel to the preferential fiber direction of the tissue membrane. Optionally, the free edge of the leaflets may also be cut with a parabolic or other curved profile to compensate for the downward angle from the commissural leaflet attachment point to the central coaptation point and to increase the total contact surface between the coapting leaflets. This approach minimizes focal weaknesses in the operating margins of the leaflet assembly and advantageously distributes the principal loading forces of the operating valve along the long axis of the collagen fibers. As a result, the tissue is resistant to surface fracture and fraying. As shown in FIG. 3, optional sizing at 320 is performed after the drying at 304 and inspection at 316.

Figure 4:
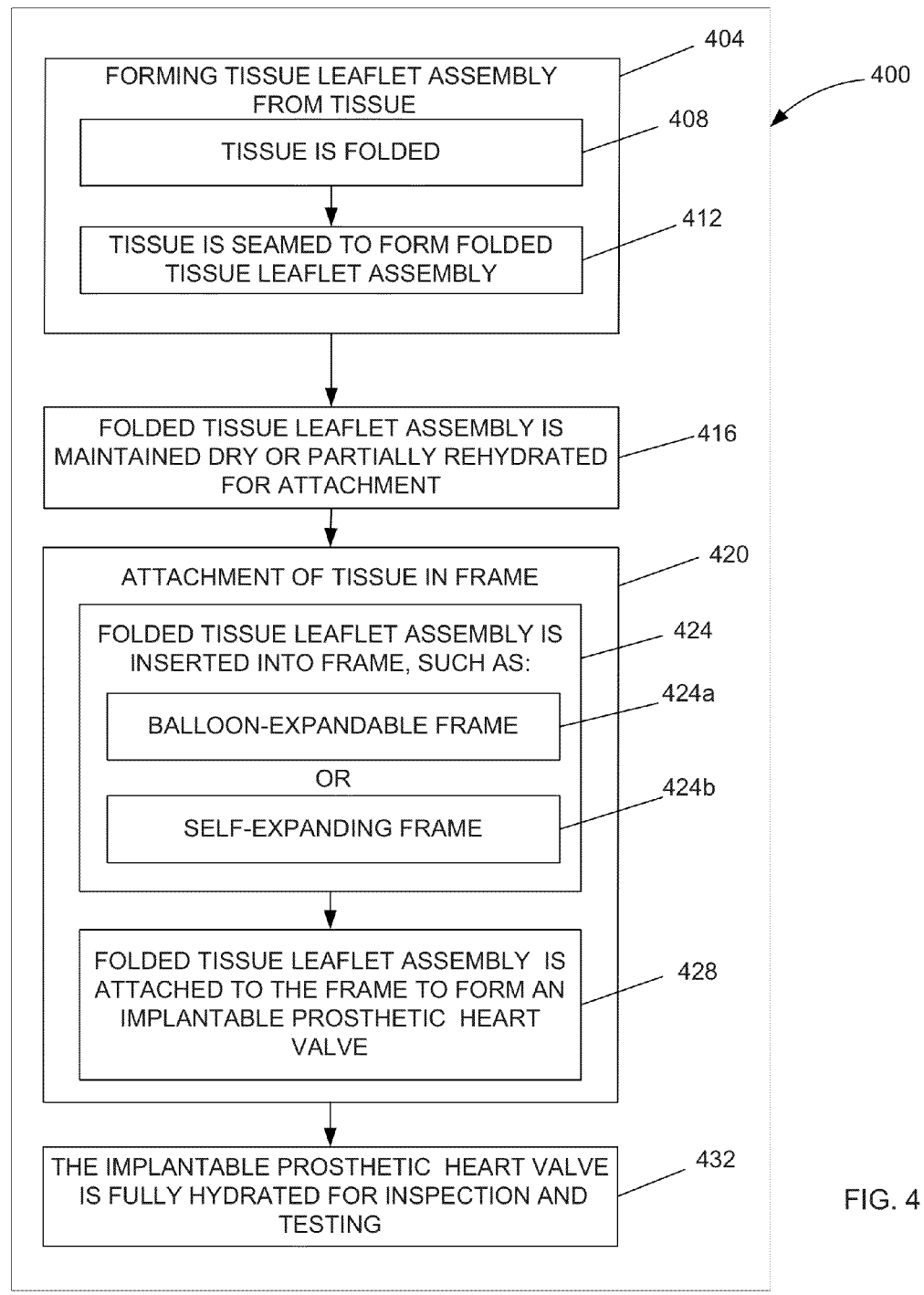
FIG. 4 is a flow chart illustrating elements of the valve construction with attachment of tissue membrane leaflets to a frame.
Figure 8A:
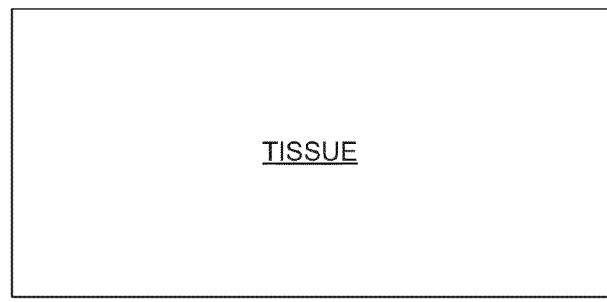
FIG. 8A is a view of a one-piece section of tissue prior to being folded.
Figure 8B:
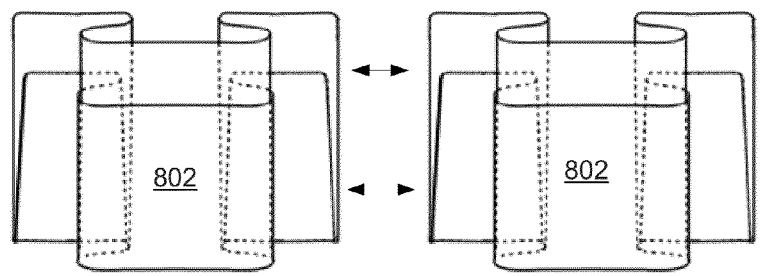
FIG. 8B is a view of two (of three) separate pieces of tissue after folding (detailed below)
Figure 8C:
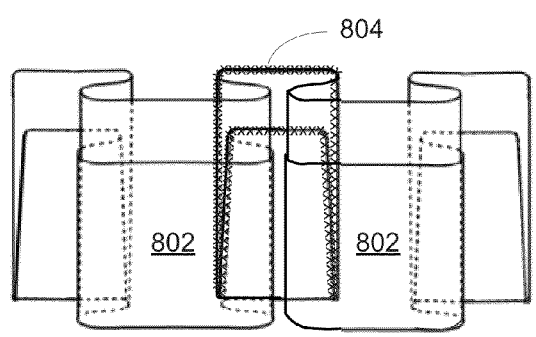
FIG. 8C is a view of the two pieces of tissue shown in FIG. 8B after being sutured together at the pleat formed after folding (detailed below)

With reference now to FIG. 4, an embodiment associated with forming a tissue leaflet assembly and attachment to a frame to form a prosthetic heart valve at 400 is further described. It is to be understood that the tissue generated from one or more of the tissue preparation procedures described herein may be used for a variety of devices or uses, and that use in a prosthetic heart valve is but one possible application for utilizing the tissue. For example, the tissue may be used in a shunt, or as graft material for repair or modification of one or more human organs, including the heart and its blood vessels. By way of further example, the tissue may be used as a pericardial membrane patch for repair of congenital heart defects. The tissue also has application as a prosthetic tissue in tendon and ligament replacement, and as a tissue product for wound management. Moreover, for use in a prosthetic heart valve, the tissue may be configured in a variety of ways and attached to a frame in a variety of ways. By way of example and not limitation, in at least one embodiment, the prepared tissue is formed into a tissue leaflet assembly at 404 by folding the tissue at 408, preferably while the tissue is in a dry state, to form at least a portion of the tissue leaflet assembly. Here, those skilled in the art will appreciate that a completed tissue leaflet assembly may be formed of a single monolithic piece of tissue 800, such as that shown in FIG. 8A, or alternatively, as shown in FIGS. 8B and 8C, it may be formed of a plurality of tissue pieces 802 that are operatively connected, such as by gluing or sewing the tissue pieces together along seams 804. As seen in FIG. 8C, the seams 804 are preferably situated at overlapping portions of pleats 832 of the plurality of tissue pieces 802.

As those skilled in the art will further appreciate, a single monolithic piece of tissue 800 or a plurality of tissue pieces 802 may be used to form a prosthetic heart valve, wherein the tissue leaflet assembly is not a folded construct. By way of example and not limitation, a plurality of separate tissue pieces may each be attached to a frame (such as by suturing) to form a prosthetic heart valve. Thereafter, whether the prosthetic heart valve is made of a folded tissue leaflet assembly or a plurality of separate tissue pieces attached to a frame, the resulting prosthetic heart valve may then be further manipulated for delivery as a dry prosthetic heart valve.

In an alternative embodiment, tissue generated from one or more of the tissue preparation procedures described herein may be used to form a prosthetic heart valve that includes a frame, and that may be implanted by a "trans-apical" approach in which the prosthetic heart valve is surgically inserted through the chest wall and the apex of the heart.

In yet another alternative embodiment, tissue generated from one or more of the tissue preparation procedures described herein may be used to form a prosthetic heart valve that does not include a frame, and is not delivered via a catheter, but rather, is implanted via a surgical opening through the patient's chest. In such a case, the prosthetic heart valve may be packaged for delivery as a dry prosthetic heart valve.

In still yet another alternative embodiment, tissue generated from one or more of the tissue preparation procedures described herein may be used to form a prosthetic heart valve that includes a frame, but that is not delivered via a catheter, but rather, is implanted via a surgical opening through the patient's chest. In such a case, the prosthetic heart valve may be packaged for delivery as a dry prosthetic heart valve.

As a further alternative to the embodiments described herein, tissue may be implanted in a "wet" or hydrated state. For example, a prosthetic heart valve utilizing a prepared tissue described herein may be packaged for delivery as a hydrated prosthetic heart valve. Accordingly, while a portion of the tissue preparation process may include drying the tissue so that it may be manipulated more easily, the tissue may then be hydrated at a later point in time prior to implantation, and it may be maintained in a hydrated condition up to and including packaging, delivery and implantation into a patient. Advantages associated with using a folded tissue leaflet assembly include that a folded structure allows a relatively thin membrane to be used by avoiding suture lines in loaded, dynamically active surfaces. Accordingly, a sutureless leaflet assembly preserves long-term integrity. However, it is to be understood that a prosthetic heart valve that does not include a folded tissue leaflet assembly is encompassed by one or more embodiments described herein.

Figure 8D:
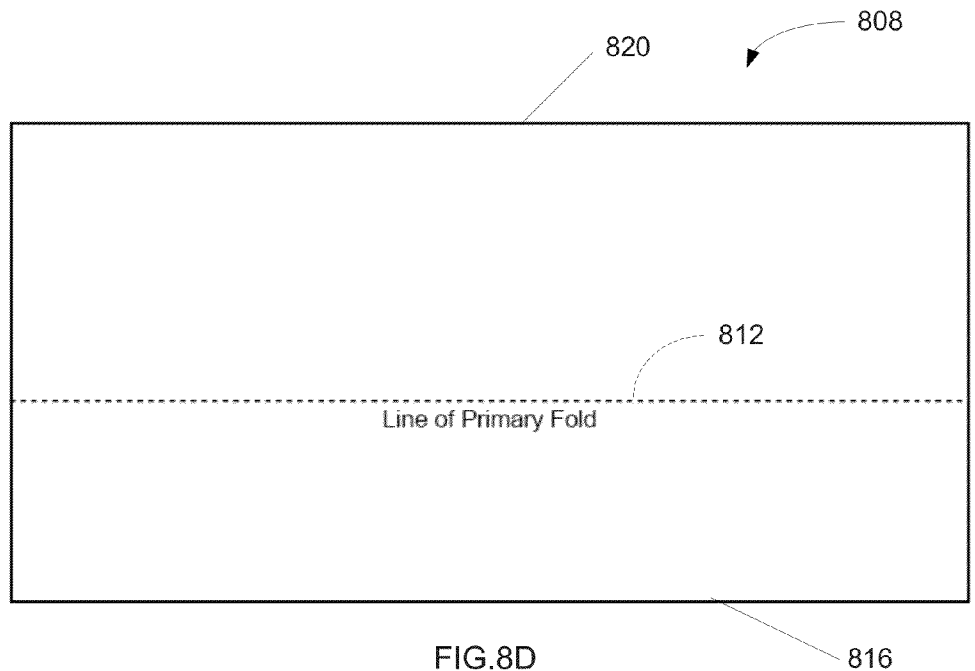
FIG. 8D is a view of a tissue blank with the line of primary fold shown using a dashed line.
Figure 8E:
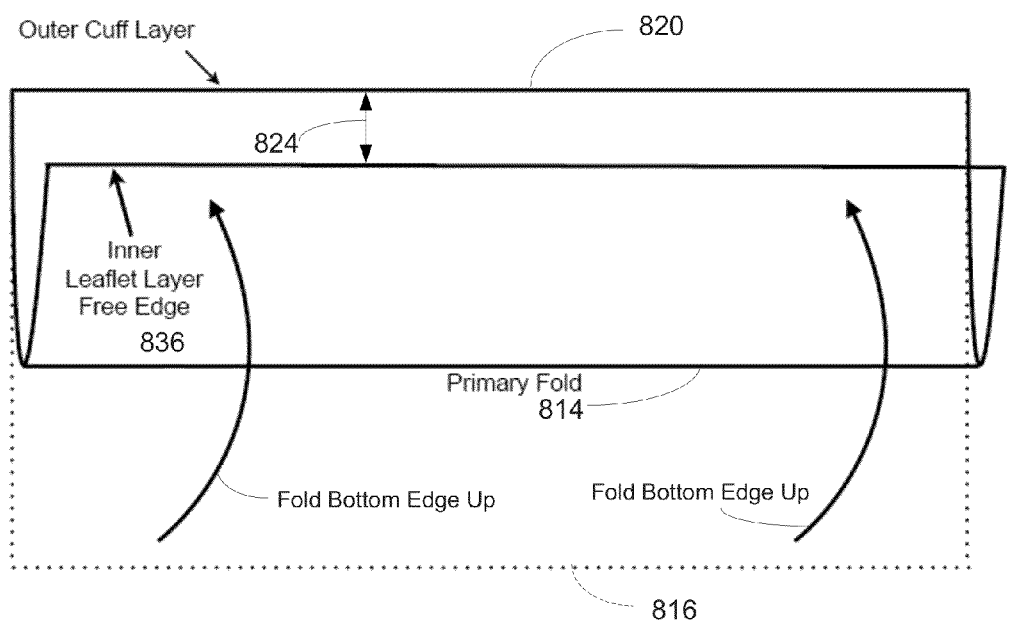
FIG. 8E is a perspective view of the tissue blank being folded along the primary fold line.

With reference now to FIGS. 8D-8L, and in accordance with at least one embodiment, for a prosthetic heart valve that includes a tissue leaflet assembly formed of a folded tissue membrane, the folding sequence for the tissue is shown for configuring the tissue into a completed tissue leaflet assembly. More particularly, a tissue blank 808 is shown in FIG. 8D, wherein the tissue blank 808 is a single monolithic piece of tissue 800. Depending upon the size requirements for a given tissue leaflet assembly, a line of primary fold or fold line 812 (shown as a dashed line) is visualized for the tissue blank 808. As shown in FIG. 8D, the primary fold 814 is achieved along the fold line 812 by folding the bottom edge 816 of the tissue blank 808 toward the top edge 820, but leaving a cuff portion 824 along the upper portion 828 of the tissue blank 808. Here, it is noted that the direction of top and bottom are relative to each other and are used as a convenience for describing the folding sequence, wherein such directions correspond to the orientation of the page illustrating the drawings. Advantageously, the folding geometry of FIGS. 8D-8L forms cuffs 824 that are continuous with the leaflets, thereby reducing the risk of aortic insufficiency or leakage.

Figure 8F:
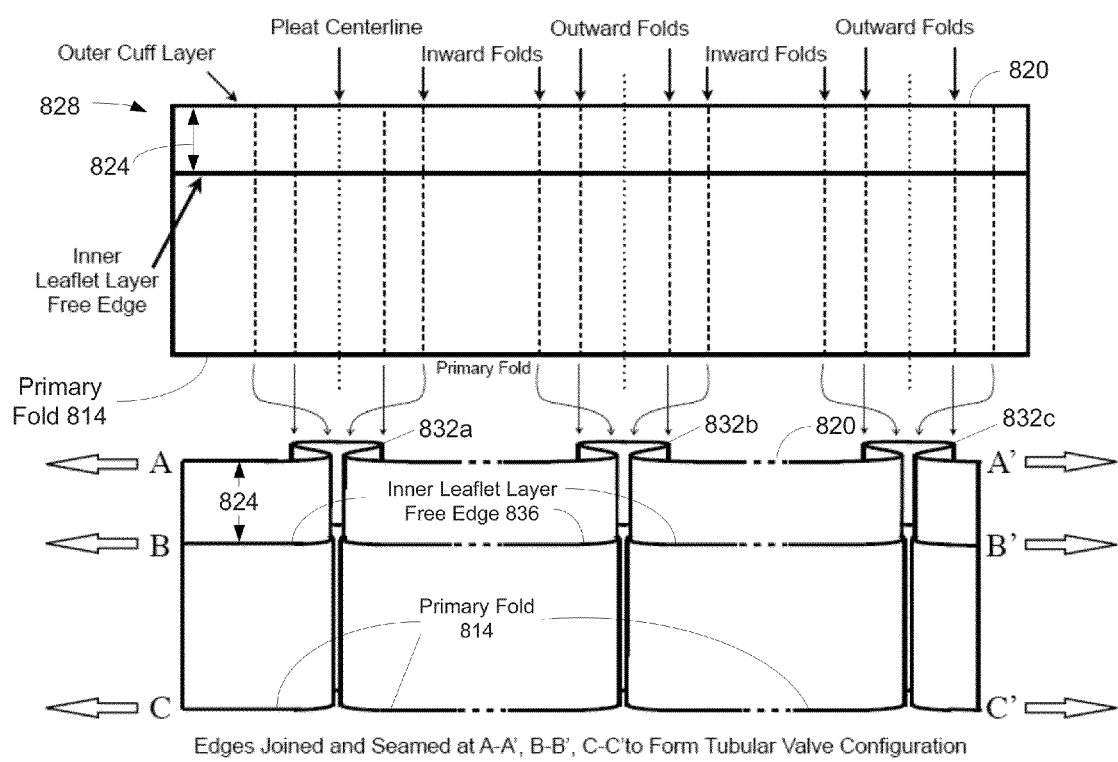
FIG. 8F is a 2-part figure showing the pleats fold lines and pleats after folding.
Figure 8G:
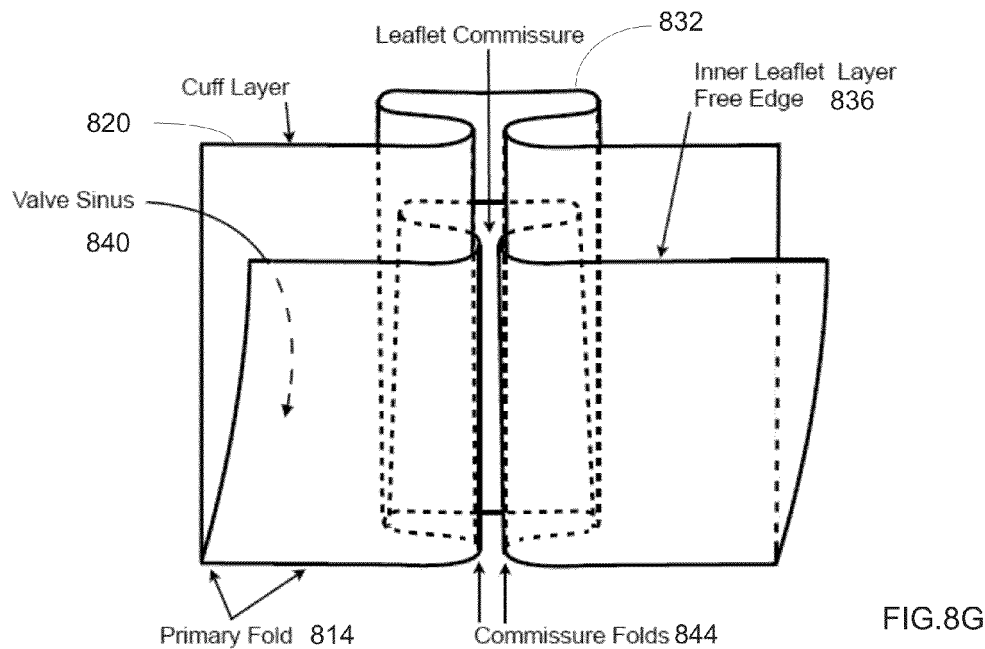
FIG. 8G is a detail perspective view of a single pleat shown in FIG. 8F.

With reference now to FIG. 8F, after folding the tissue blank 808 along fold line 812 to form primary fold 814, pleats are formed by folding the tissue along its length. For the embodiment shown in FIG. 8F, three pleats 832a, 832b, and 832c are shown. FIG. 8G illustrates a detail drawing of a single pleat 832 representative of one of pleats 832a-c. In FIG. 8G, the inner leaflet layer free edge 836 is shown, as is the valve sinus 840 and the commissure folds 844.

Figure 8H:
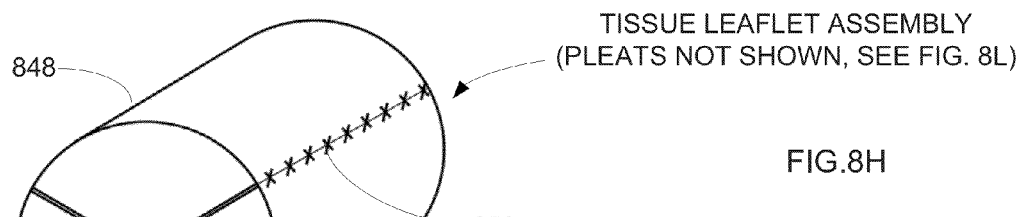
FIG. 8H is a perspective schematic view of a folded and seamed tissue leaflet assembly.
Figure 8I:
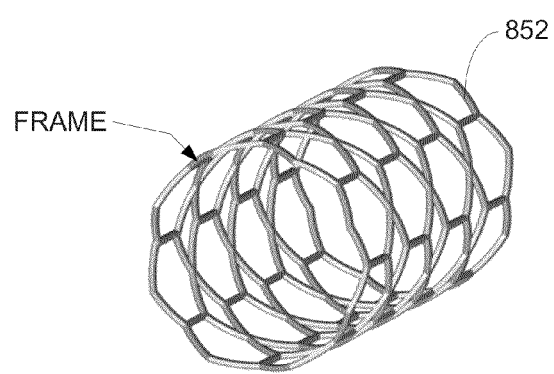
FIG. 8I is a perspective schematic view of a frame.
Figure 8J:
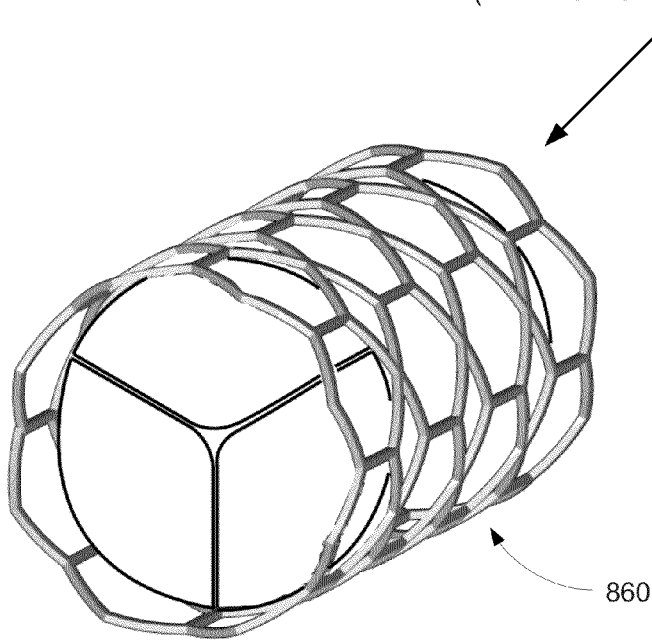
FIG. 8J is a perspective schematic view of the frame of FIG. 8I with the tissue leaflet assembly of FIG. 8H attached thereto.
Figure 8K:
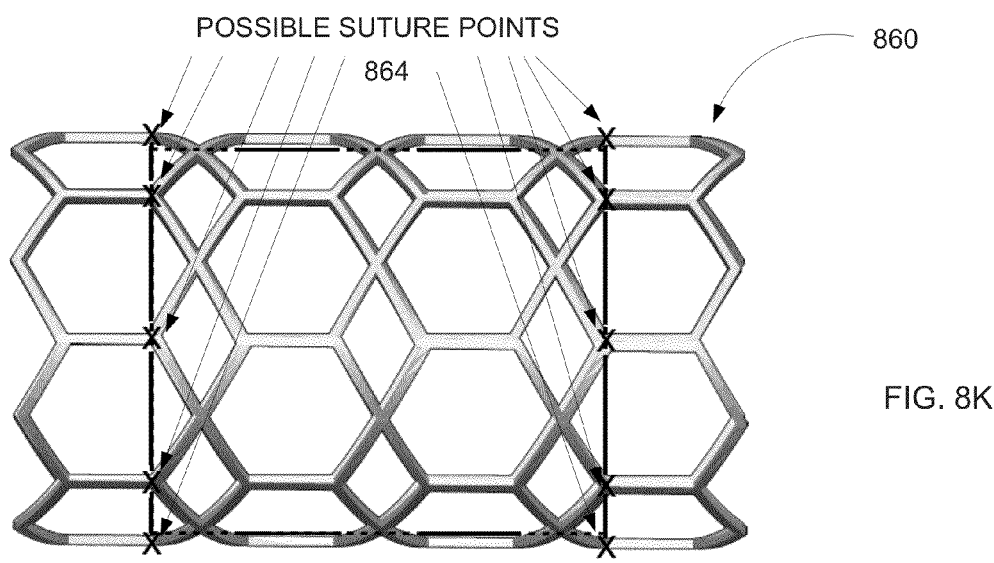
FIG. 8K is side elevation schematic view of the device shown in FIG. 8J.
Figure 11A:
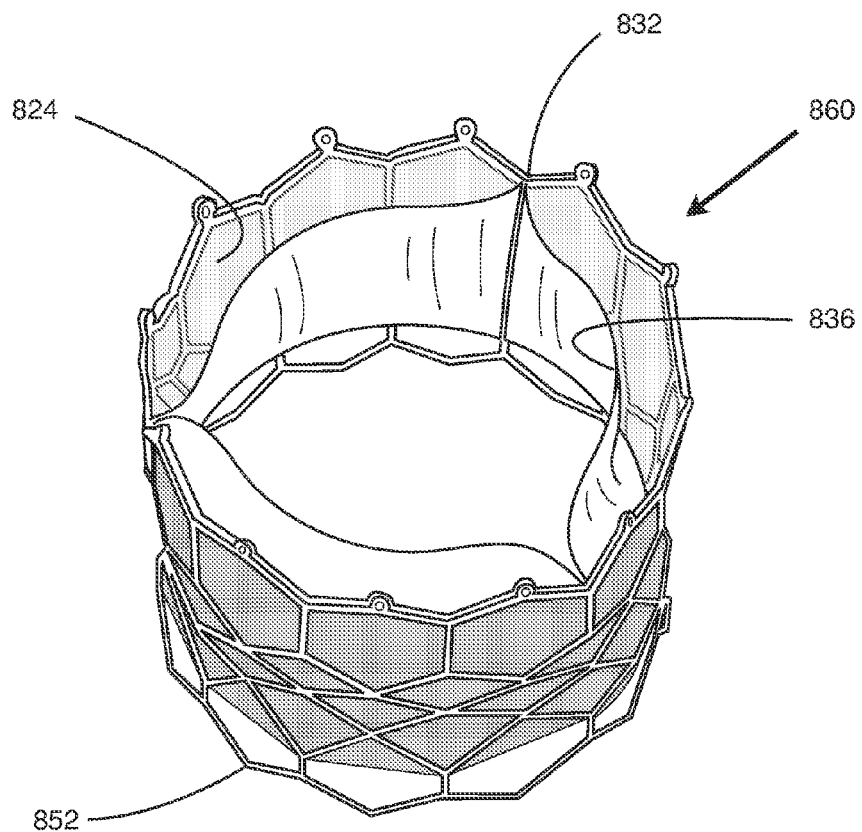
FIG. 11A is a photo of an implantable prosthetic heart valve, including a tissue leaflet assembly attached within a frame, wherein the tissue is situated in a partially open orientation.
Figure 11B:
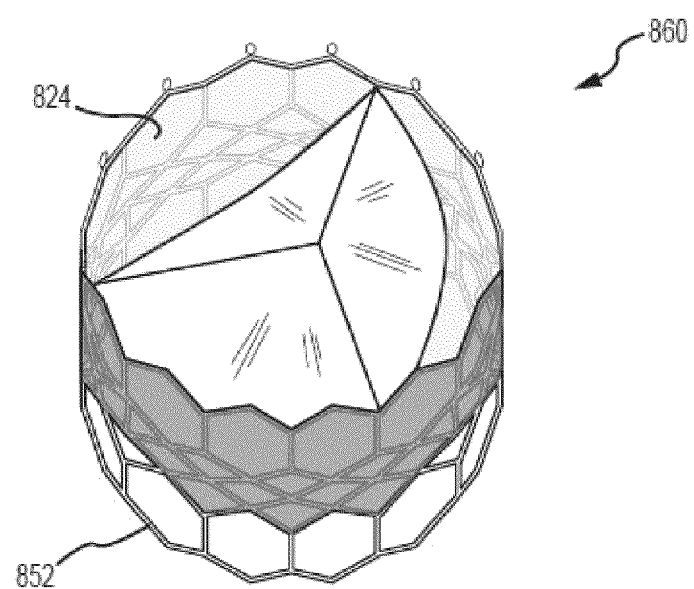
FIG. 11B is a drawing of an implantable prosthetic heart valve, including a tissue leaflet assembly attached within a frame, wherein the tissue is situated in a closed orientation.

Referring again to FIG. 4 as well as FIG. 8H, at 412 the folded tissue is seamed to form a folded tissue leaflet assembly. More particularly, FIG. 8H shows a schematic perspective drawing of tissue leaflet assembly 848, wherein the pleated tissue construct shown in the bottom half of FIG. 8F is seamed, such as along seam 850, to form a substantially tubular construct. At 416, the folded tissue leaflet assembly 848 is maintained dry or is partially hydrated prior to mounting the tissue leaflet assembly in a frame. At 420, the tissue leaflet assembly 848 is then attached within a frame, such as frame 852 shown in FIG. 8I. The tissue leaflet assembly 848 attached within a frame 852 forms an implantable prosthetic heart valve 860, such as that shown in the schematic perspective drawing of FIG. 8J, side elevation view FIG. 8K, as well as that shown in the photo of FIG. 11A, and drawing of FIG. 11B. FIG. 8K illustrates possible suture points 864 where the tissue leaflet assembly 848 can be sutured to the frame 852. That is, the tissue leaflet assembly 848 may be attached within the frame 852, such as by suturing the outer layer of the tissue leaflet assembly 848 to the frame. In the foregoing sentence, and as used herein, it is noted that the term "attached" means that the tissue leaflet assembly 848 is secured to the frame 852, although the inner leaflet layer free edges 836 are able to readily move during operation of the prosthetic heart valve 860.

Figure 11C:
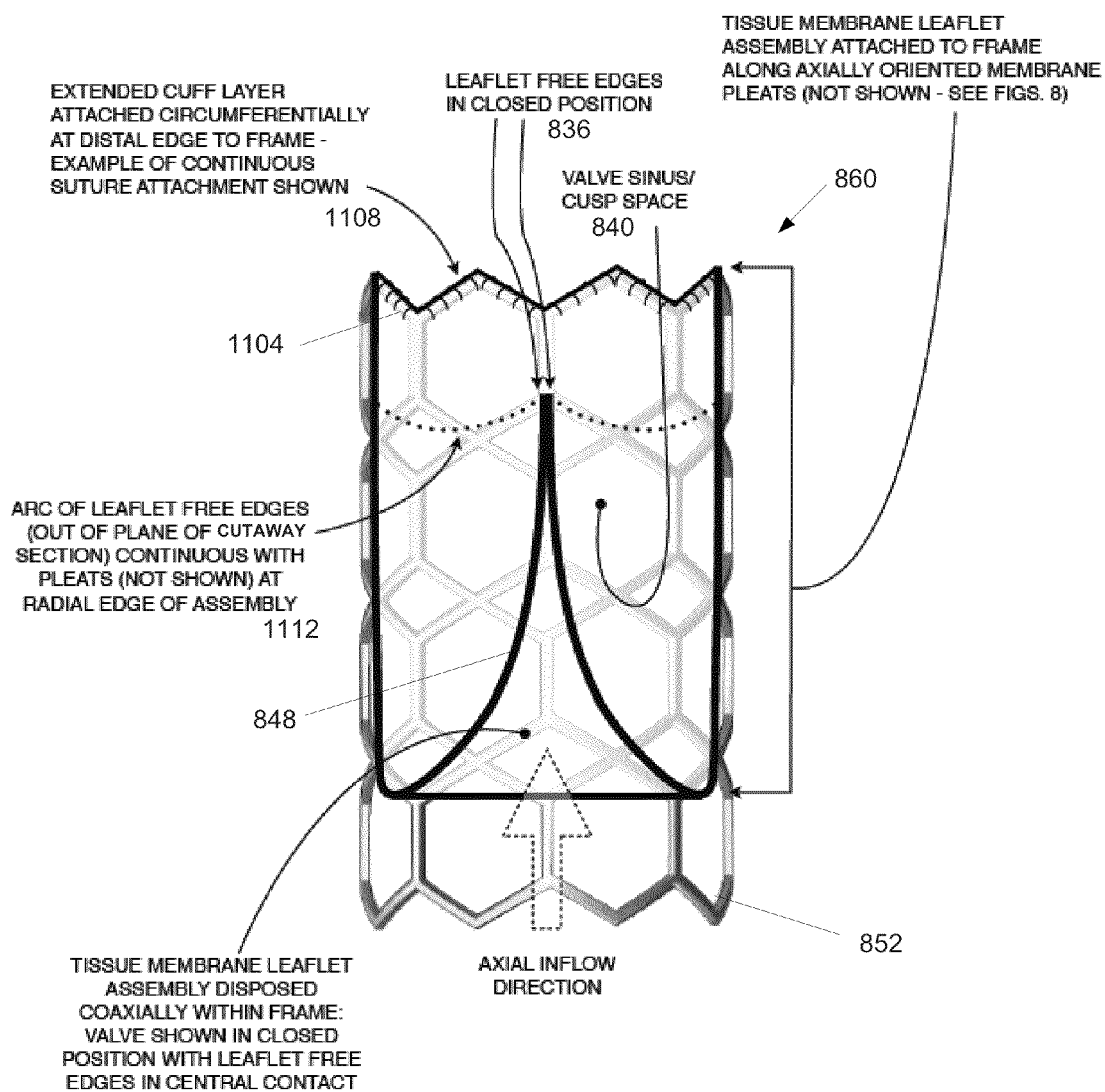
FIG. 11C is a side cutaway view of an implantable prosthetic heart valve, including a tissue leaflet assembly attached within a frame, wherein the tissue is situated in a closed orientation.

Referring now to FIG. 11C, a cutaway side elevation view of a prosthetic heart valve 860 that includes a frame 852 with a tissue leaflet assembly 848 attached therein is shown. The tissue membrane leaflet assembly 848 is disposed coaxially within the frame 852. As shown in FIG. 11C, the valve 860 is illustrated in the closed position with the leaflet free edges 836 in at least partial contact with each other. An arc 1112 of the leaflet free edges 836 (out of plane of the cutaway view) is continuous with pleats 832 at the radial edge of the tissue leaflet assembly 848, and may be seen in the alternate view shown in FIG. 8L. The tissue membrane leaflet assembly 848 is attached to the frame 852 along the axially oriented membrane pleats 832, as illustrated again in FIG. 8L. The extended cuff layer is attached circumferentially at the distal edge 1104 of the frame 852. By way of example and not limitation, continuous suture attachment 1108 may be used to attach the extended cuff layer to the distal edge 1104.

Figure 11D:
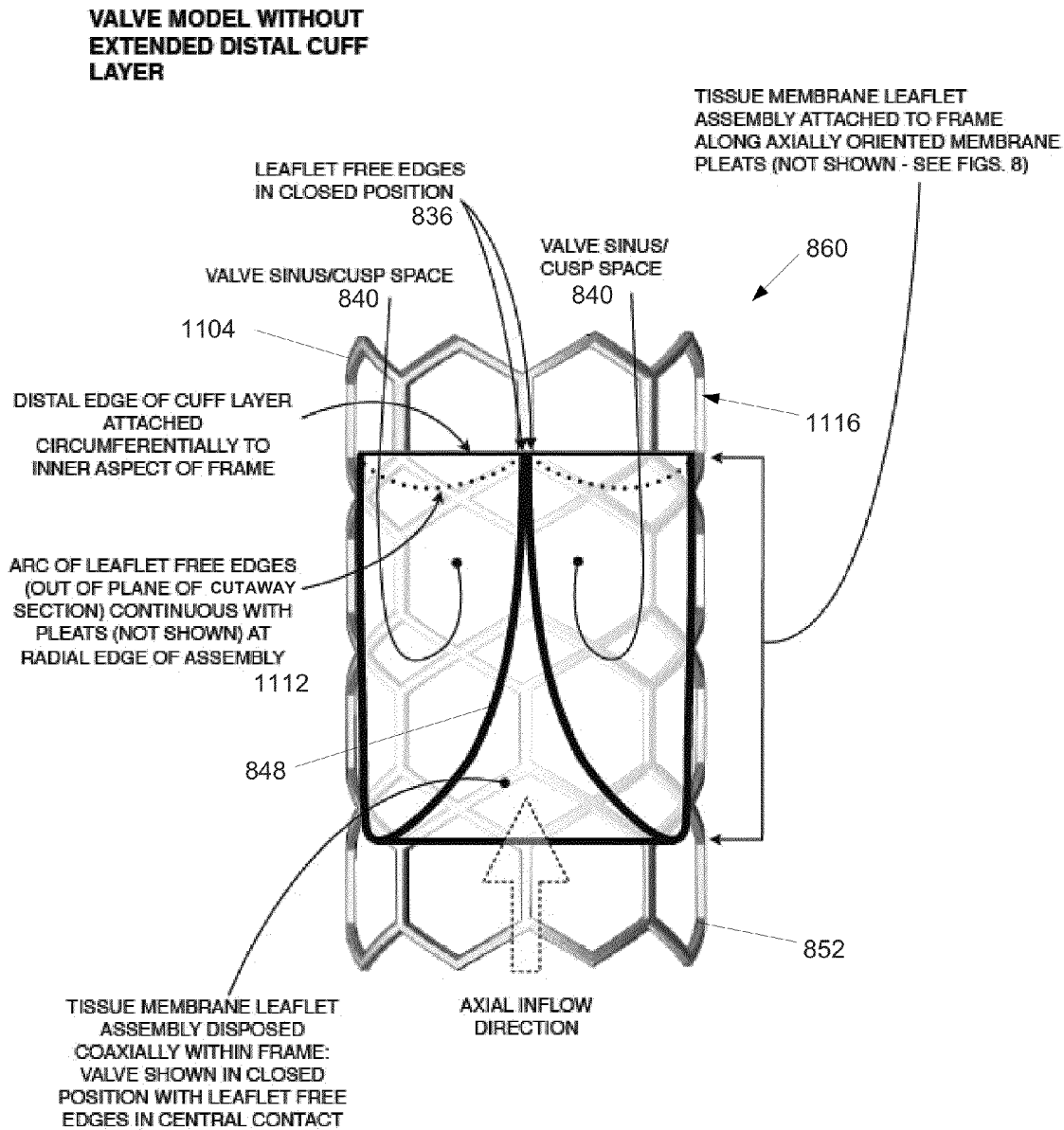
FIG. 11D is another side cutaway view of an implantable prosthetic heart valve, including a tissue leaflet assembly attached within a frame, wherein the tissue is situated in a closed orientation.

Referring now to FIG. 11D, an embodiment is shown wherein the cuff layer is not extended distally to the distal edge 1104 of the frame 852. As shown in FIG. 11D, the distal edge of the cuff layer is attached circumferentially to an inner aspect of the frame 852, such as along those possible suture points 864 illustrated in FIG. 8K. As a result, a distal portion 1116 of the frame 852 does not include any portion of the tissue leaflet assembly 848, such as the cuff layer. However, with the valve 860 in the closed position the leaflet free edges 836 still at least partially contact each other.

Figure 8L:
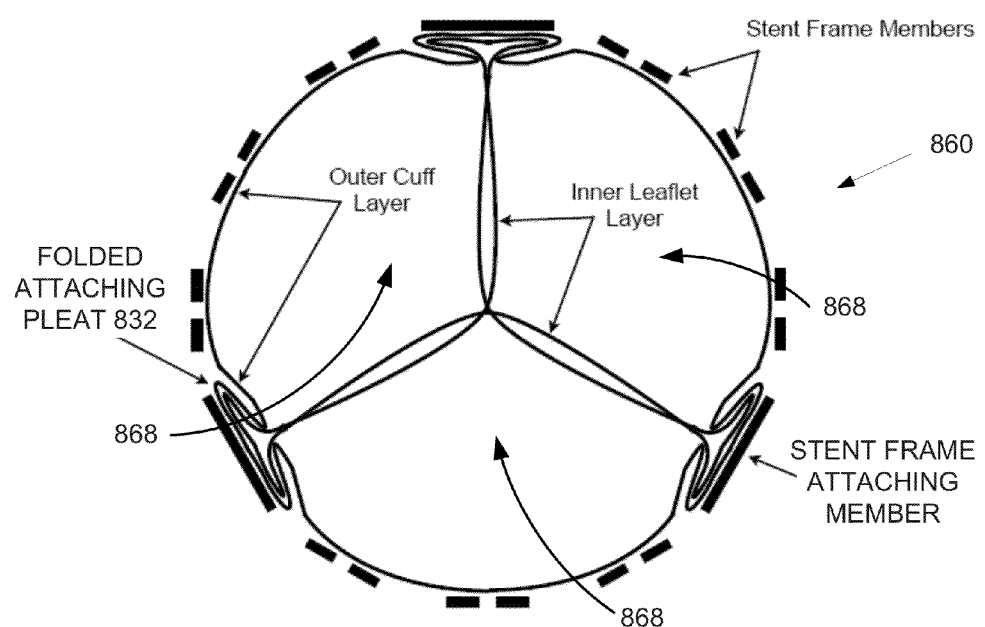
FIG. 8L is an end schematic view of the frame and tissue leaflet assembly attached thereto.
Figure 12:
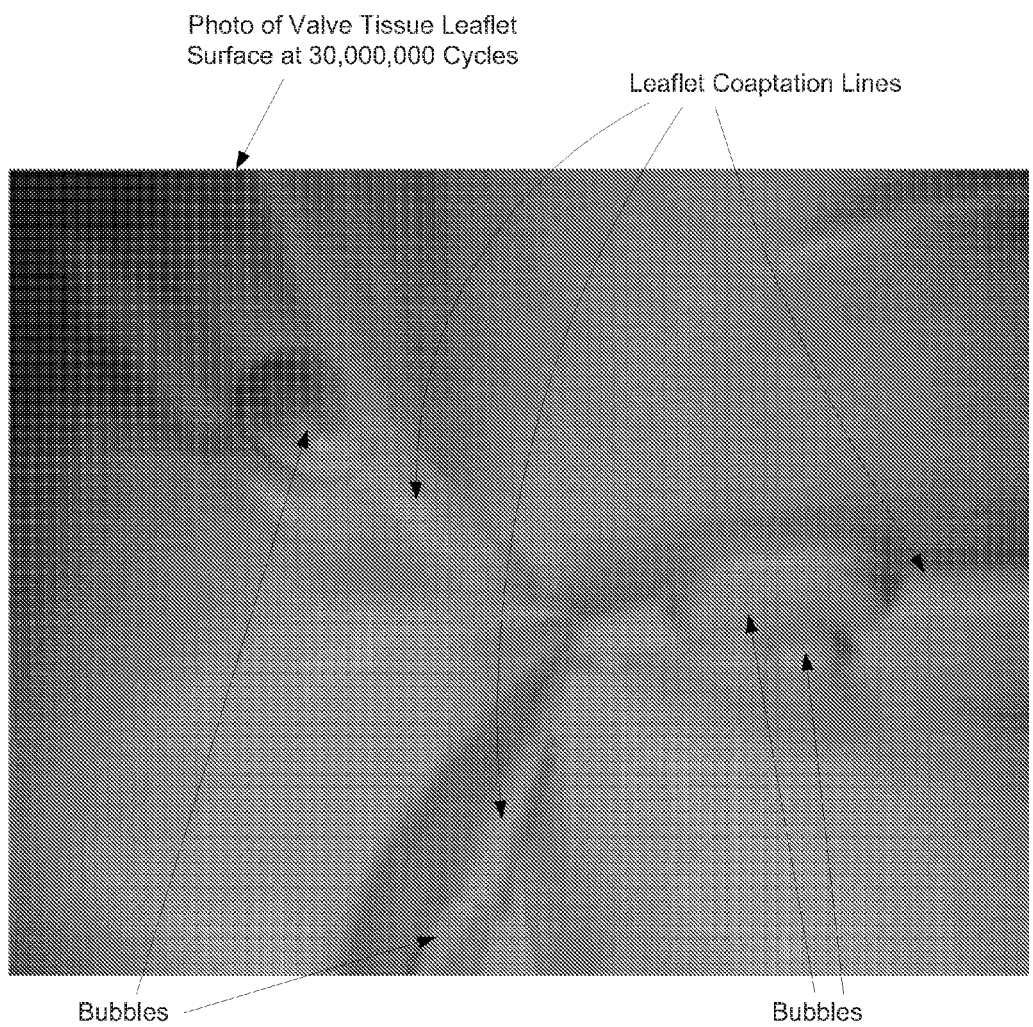
FIG. 12 is a photo of valve tissue after testing through 30,000,000 cycles of pumping used to model human heart conditions, wherein the photo shows a smooth uniform surface.

With reference now to FIG. 8L, an end view of the prosthetic heart valve is shown. As depicted in FIG. 8L, the pleats 832 are used as the portion of the tissue leaflet assembly 848 to attach to the frame 852. As can be seen in FIG. 8L, the outer cuff layer is attached to the frame members of frame 852. When the prosthetic heart valve 860 is closed, the cusps 868 formed by the inner leaflet layer are generally situated as depicted in FIG. 8L. FIG. 12 is a photo of the tissue leaflets of a prosthetic heart valve after 30,000,000 cycles of testing to model performance if associated with a human heart. In testing, the prosthetic heart valve 860 has demonstrated a natural opening gradient of approximately 5 mmHg.

It will be appreciated by one of ordinary skill in the art that the tissue leaflet assembly 848 described and shown herein is but one possible construct for forming a flow control mechanism that can be attached to a frame to regulate the flow of blood in a patient's vascular system upon deployment. That is, the illustrated tissue leaflet assembly 848 is provided by way of example and not limitation, and in no way should be interpreted to limit the geometries of membrane leaflet assemblies that can be used to regulate fluid flow. Accordingly, other leaflet configurations and constructs are considered encompassed by claims directed to or otherwise including premounted percutaneously deliverable valves.

As those skilled in the art will appreciate, the frame 852 may be a stent or a structure having similarities to a stent. The frame 852 essentially serves as a holding mechanism for the tissue leaflet assembly 848 that can then be inserted percutaneously into a patient, wherein the frame 852 serves as a way to anchor the folded tissue leaflet assembly 848 to a vascular portion (e.g., in situ arterial tissue) of the patient. Thus, at 424 the tissue leaflet assembly 848 is inserted into a frame 852. More particularly, at 424a the frame 852 may comprise a balloon-expandable frame, or alternatively, at 424b a self-expanding frame may be used. After the tissue leaflet assembly is inserted into the frame, at 428 the folded tissue leaflet assembly 848 is attached to the frame 852, such as by suturing the tissue leaflet assembly 848 to the frame 852 to form an implantable prosthetic heart valve 860, such as that shown in FIG. 8L. In at least one embodiment, after attaching the tissue leaflet assembly 848 within the frame 852 and connecting the tissue leaflet assembly 848 to the frame 852 to form an implantable prosthetic heart valve 860, at 432 the prosthetic heart valve 860 is fully hydrated for inspection and testing. Thereafter, the fully constructed implantable prosthetic heart valve 860 may be dried and maintained in a substantially dry condition. Accordingly, as those skilled in the art will appreciate, one or more embodiments described herein provide a tissue 800 suitable for implanting in a human, wherein the implantable tissue may be allowed to dry prior to implanting, or it may be hydrated prior to implanting. In addition, the tissue 800 is suitable for use in forming a tissue leaflet assembly 848 for use in a prosthetic heart valve, including an implantable prosthetic heart valve 860 that can be implanted with its tissue leaflet assembly in a dry state, or with its tissue leaflet assembly in a partially or fully hydrated state.

One or more of the embodiments of the tissue leaflet assemblies described herein may be implanted into the patient using a balloon-expandable frame or a self-expanding frame. Expandable frames are generally conveyed to the site of the target valve on balloon catheters. For insertion, the expandable frame is positioned in a compressed configuration along the delivery device, for example crimped onto the balloon of a balloon catheter that is part of the delivery device intended for coaxial mounting on a guidewire. After the expandable frame is positioned across the plane of the valve, the expandable frame is expanded by the delivery device. For a self-expanding frame, commonly a sheath is retracted, allowing expansion of the self-expanding frame.

In at least one embodiment, the frame comprises a metal alloy frame possessing a high strain design tolerance that is compressible to a relatively small diameter. By providing a device with a low profile, the implantable prosthetic heart valve 860 allows standard retrograde arterial aortic delivery via femoral artery insertion, without surgical cutdown or general anesthesia. This is achieved by providing the prosthetic heart valve on a premounted delivery system with the tissue leaflet assembly or tissue membrane construct in a substantially dry condition.

In accordance with one or more embodiments, a dry tissue membrane has substantially less mass than a wet membrane. By way of example, a substantially dry pericardium tissue prepared by one or more of the present embodiments has approximately 30% of the mass of a wet pericardium tissue, and marked reduction in profile and packing volume, thereby achieving a relatively low profile and making it suitable for implantation in greater number of patients, especially those having small diameter vascular systems. In addition, a dry prosthetic heart valve does not require storage and transport in preservative. A dry prosthetic heart valve can be mounted on a delivery catheter at its location of manufacture, which allows for pre-packaging of an integrated delivery system. In the foregoing sentence, it is noted that the term "mounted" means that the prosthetic heart valve 860 is temporarily associated with the delivery catheter. Together with a relatively low profile, embodiments of the prosthetic heart valve thereby offer reliability and convenience because the implantable prosthetic heart valve 860 is pre-mounted upon its delivery catheter and forms part of a pre-packaged delivery system. In addition, a dry prosthetic heart valve does not require rinsing, rehydration, or mounting in a catheterization lab. Therefore, a dry prosthetic heart valve can be inserted directly from package into the patient's body at a critical time during the procedure. Advantageously, this avoids procedure time, manipulation, and errors of mounting, crimping, and orienting catheters and sheaths. Once at the surgical facility/location, the dry prosthetic heart valve is inserted and delivered by balloon catheter expansion in the plane of the target valve in the standard way and the dry prosthetic heart valve begins to function immediately, even without specific steps to rehydrate the tissue membrane portion of the heart valve from its dry state, with hydration of the tissue membrane subsequently occurring rapidly and naturally in the body. More particularly, hydration of the tissue membrane portion occurs rapidly and begins with simple preparatory flushing of catheter lumens with saline. Thereafter, hydration continues with device insertion and dwelling into the central blood vessels, and completes naturally after deployment in the patient's body.

The low profile of the implantable prosthetic valve is particularly advantageous for patient's having relatively small diameter vascular systems. Table 1 provides aortic and pulmonary valve prosthesis sizing.

TABLE 1

Aortic and Pulmonary Valve Prosthesis Sizing

| Aorta/Pulmonary Valve Diameter | Collapsed Implantable Prosthetic Heart Valve Size (French) | Collapsed Implantable Prosthetic Heart Valve Diameter |
|---|---|---|
| 19-21 mm | 12 French | 4.0 mm |
| 22-26 mm | 14 French | 4.7 mm |
| 27-30 mm | 16 French | 5.3 mm |

For most human patients, the femoral artery has a diameter of between about 5-8 mm. Accordingly, it is apparent that embodiments of the collapsed implantable prosthetic heart valves 860 described herein offer a low profile that enables a larger group of patients to qualify for receiving an implantable prosthetic heart valve 860. As a result of the sizing advantages offered by one or more embodiments of implantable prosthetic heart valves 860 described herein, virtually no candidate patients would be excluded from treatment with an implantable prosthetic heart valve 860 without open heart surgery and without general anesthesia on the basis of inadequate femoral blood vessel access caliber. In addition, one or more embodiments of the implantable prosthetic heart valve 860 described herein feature a scalable construct, wherein the implantable prosthetic heart valves 860 can be produced to accommodate target valve diameters ranging between 6-35 mm, and wherein the implantable prosthetic heart valves 860 offer consistent function using fundamentally a single design.

Figure 5:
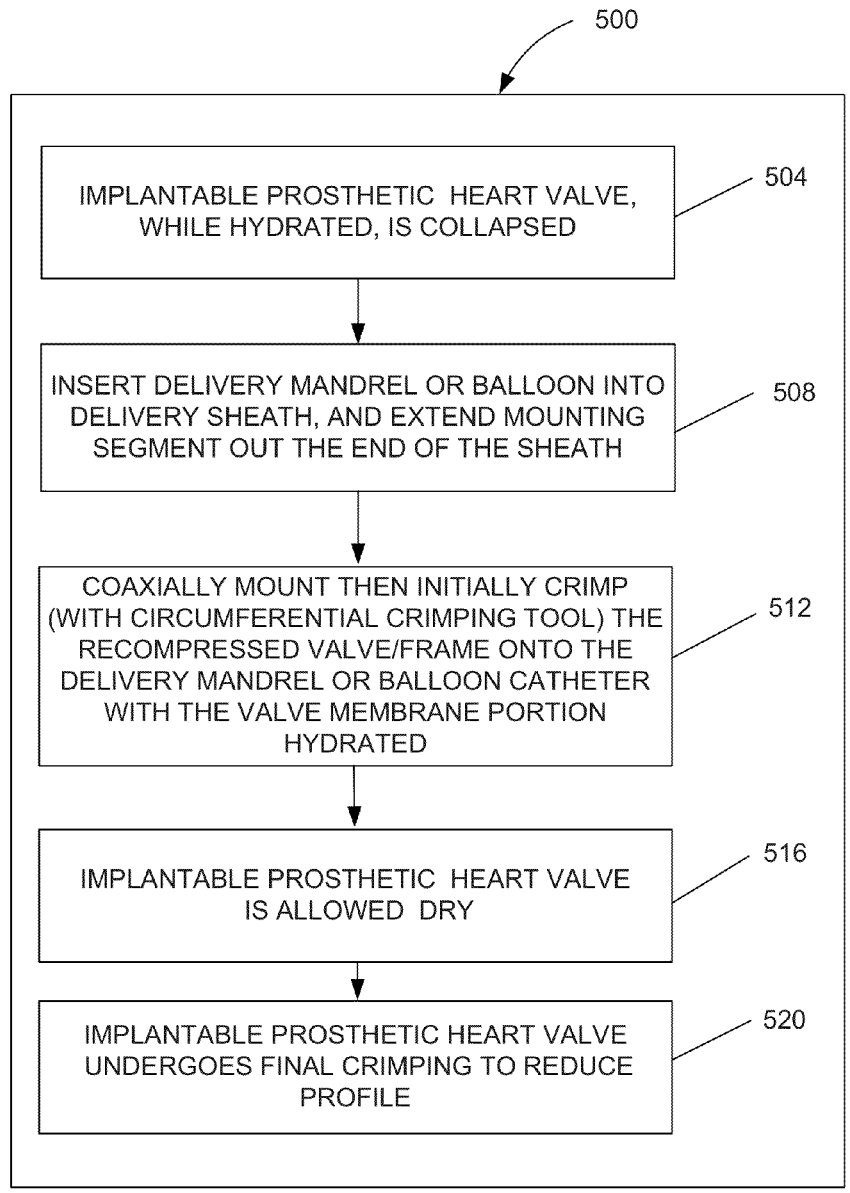
FIG. 5 is a flow chart illustrating elements of the mounting of the valve into a delivery system.

Referring now to FIG. 5, the mounting of the implantable prosthetic heart valve 860 into a delivery system at 500 is further described. More particularly, at 504 an implantable prosthetic heart valve 860 (also referred to herein as a percutaneously deliverable heart valve) is collapsed. The initial phase of collapsing the percutaneously deliverable heart valve is executed with the tissue membrane in a hydrated condition. That is, since the percutaneously deliverable heart valve 860 includes the frame 852 with the tissue leaflet assembly 848 attached within the frame 852, the percutaneously deliverable heart valve 860 is collapsed down as an integral unit. If a balloon-expandable frame is used, then an axial puller may be utilized to collapse down the frame 852 of the percutaneously deliverable heart valve 860 without the application of force directly to the sides of the frame 852. This procedure offers the advantage of preserving the cell structure of the frame 852 while also maintaining the orientation of the leaflets of the tissue leaflet assembly 848 as the percutaneously deliverable heart valve 860 is compressed. The proper orientation and disposition of the leaflets is facilitated by the hydrated state of the leaflets. This assists in preventing tissue prolapse or bulging of the tissue 800 or 802 through the frame 852. In addition, this technique reduces recompression strain on the metal frame 852 (e.g., a stent) that can tend to compromise fatigue life of the frame 852. This technique also tends to promote the circumferentially uniform collapsing of cells in the frame 852, thereby mitigating bunching of the tissue that forms the tissue leaflet assembly 848 of the percutaneously deliverable heart valve 860. For a self-expanding frame, the sides are forced to collapse by providing a radial compression force to the frame and may be assisted by axial traction force.

With further reference to FIG. 5, the percutaneously deliverable heart valve 860 (i.e., the frame 852 with the tissue leaflet assembly 848 attached thereto) is collapsed in an initially hydrated state. At 508 the delivery mandrel or balloon is inserted into a delivery sheath, and the mounting segment is then extended out the end of the sheath. Thereafter, at 512 the sheath and frame are coaxially mounted and then compressed with initial crimping onto the mounting segment with the tissue leaflet assembly 848 still in a hydrated state. At 516, the tissue leaflet assembly 848 of the percutaneously deliverable heart valve 860 is then allowed to dry, which further reduces the volume and profile of the tissue membrane leaflets, permitting further compression by radial force. Accordingly, in the final compression step, the percutaneously deliverable heart valve 860 is then further crimped with a circumferential crimping tool at 520 to finally mount the compressed valve/frame onto the delivery mandrel or balloon catheter.

Figure 6:
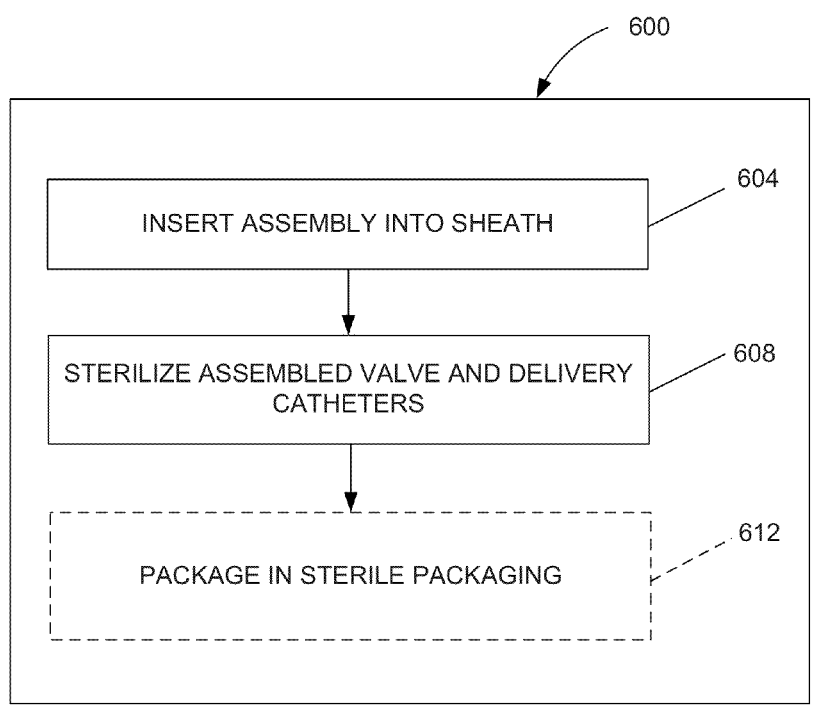
FIG. 6 is a flow chart illustrating elements of the ensheathing, sterilization, and packaging.
Figure 10:
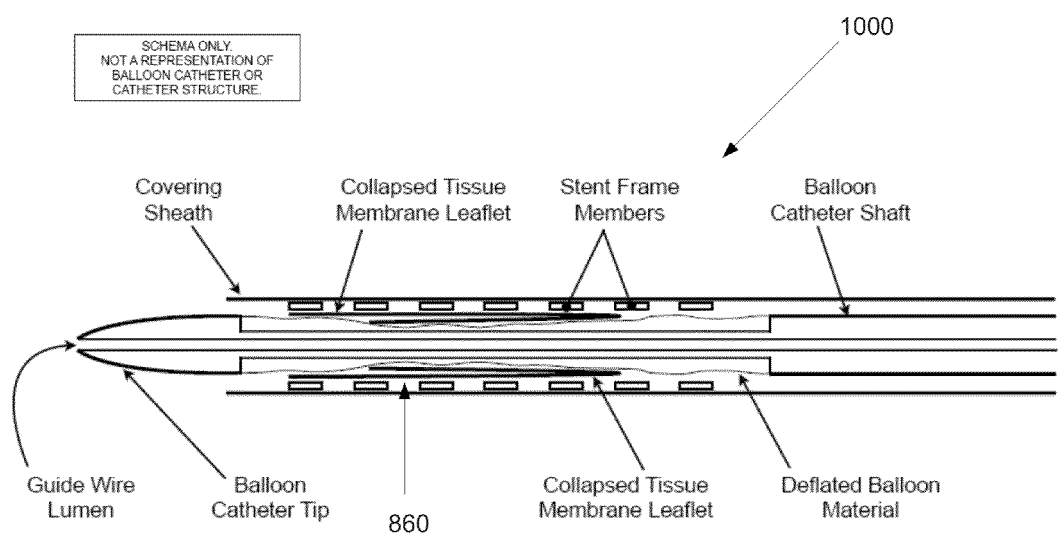
FIG. 10 is a schematic of a portion of a catheter with a percutaneously deliverable heart valve mounted thereto.

Referring now to FIG. 6, the ensheathing, sterilization and packaging at 600 is described. More particularly, once the percutaneously deliverable heart valve 860 is coaxially mounted and crimped on a delivery mandrel or balloon catheter as described above and shown in FIG. 5, the assembly is then inserted at 604 into a distal end of a delivery sheath, such as by "backloading" the assembly into position with a distal end of the percutaneously deliverable heart valve 860 contained within the delivery sheath proximate the end of the sheath. Reference here is made to FIG. 10 that schematically illustrates catheter 1000 with an implantable prosthetic heart valve 860 mounted thereto.

Figure 13:
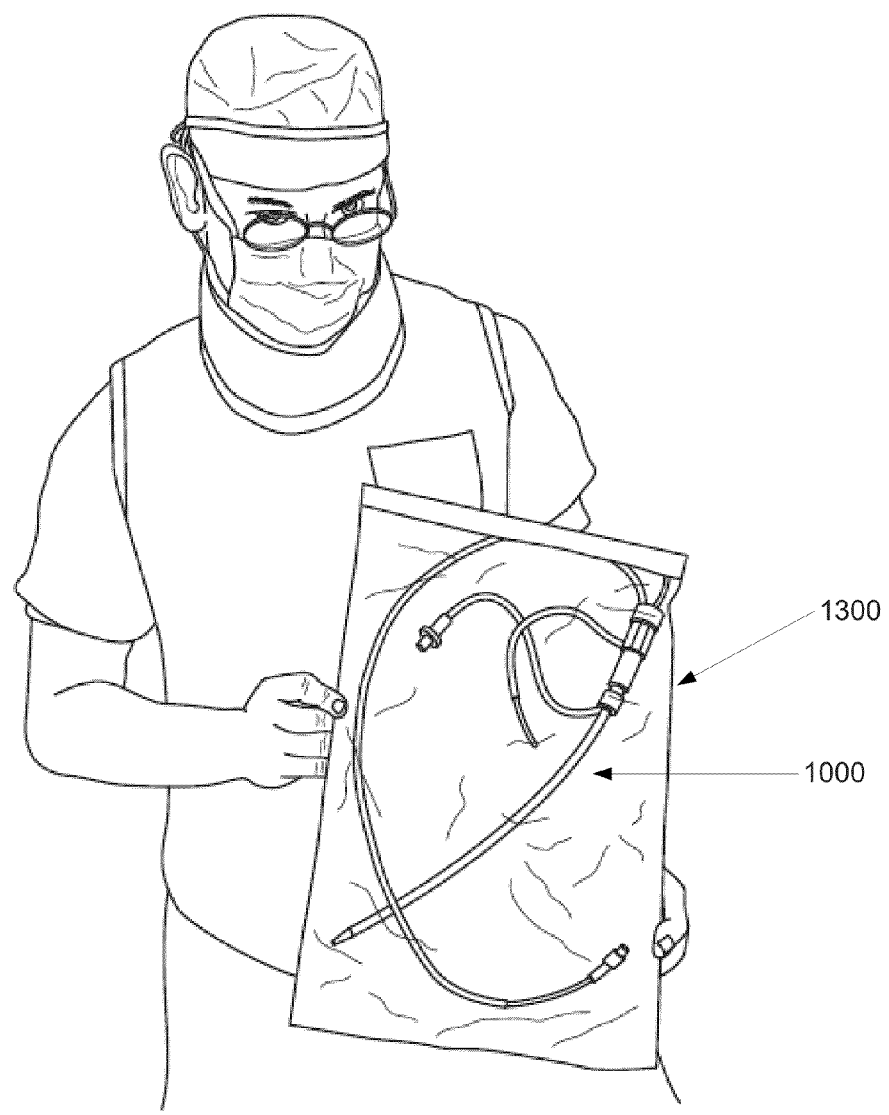
FIG. 13 is a drawing of a surgeon holding a premounted percutaneously deliverable heart valve associated with a catheter and residing within sterile packaging.

With further reference to FIG. 6, at 608 the percutaneously deliverable heart valve 860 and delivery catheters are sterilized, such as by using by one or more of ethylene oxide, proton beam, or gamma radiation. At 612, the assembly is then optionally packaged in a sterile package. Additional elements are optionally shipped with the assembly, wherein, by way of example, such elements may include any necessary delivery tools and documentation. In at least one embodiment, the package may optionally contain a device to control the water vapor content within the sealed volume of the package. FIG. 13 depicts a surgeon holding a sterile package 1300 containing a premounted percutaneously implantable prosthetic heart valve.

Figure 7:
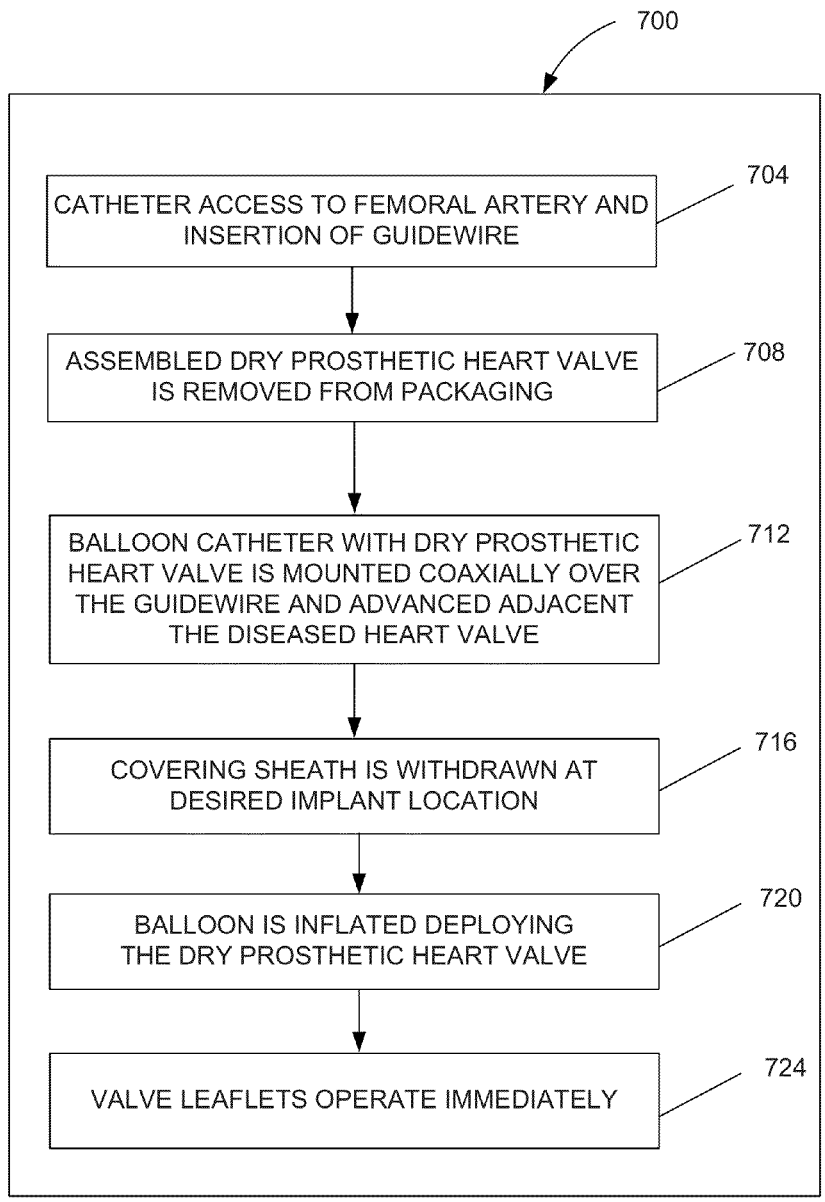
FIG. 7 is a flow chart illustrating elements of the delivery of the valve into a patient.
Figure 14:
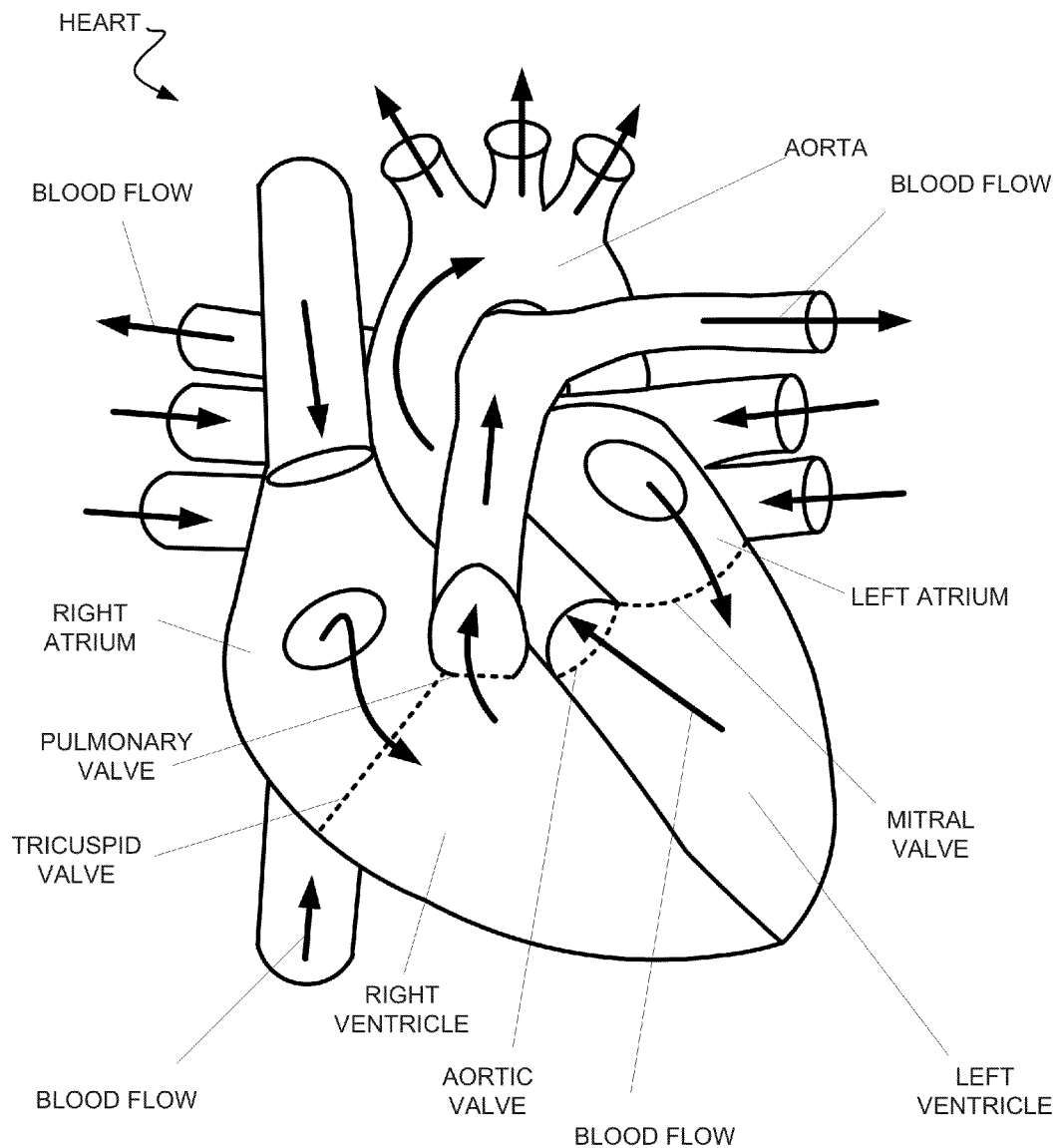
FIG. 14 is a schematic of a simplified cutaway view of a human heart, including heart valves that may be targeted for receiving an embodiment of an implantable prosthetic heart valve.
Figure 15:
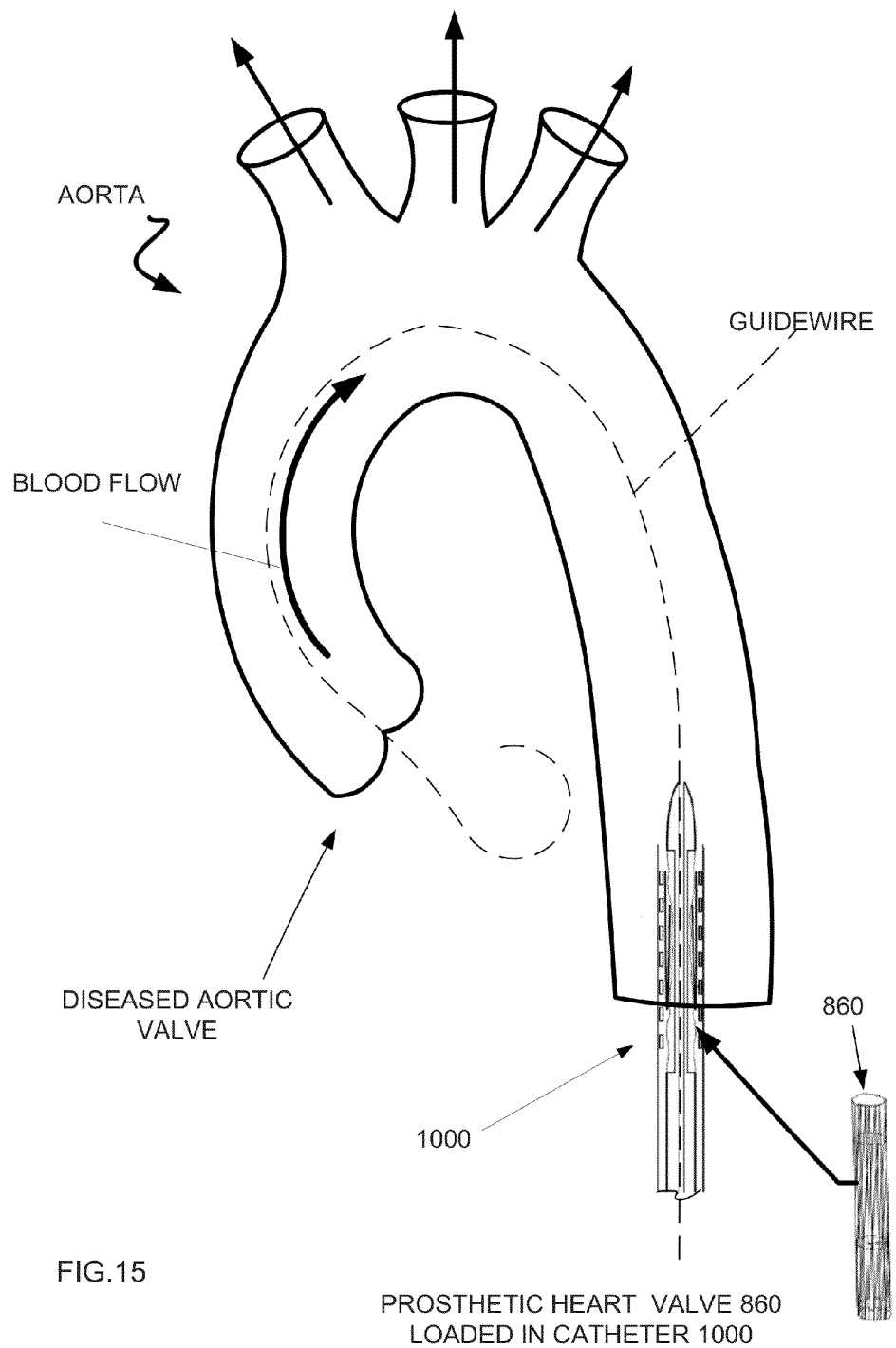
FIG. 15 is a schematic of a human aorta receiving a catheter with an implantable prosthetic heart valve mounted thereto.
Figure 16:
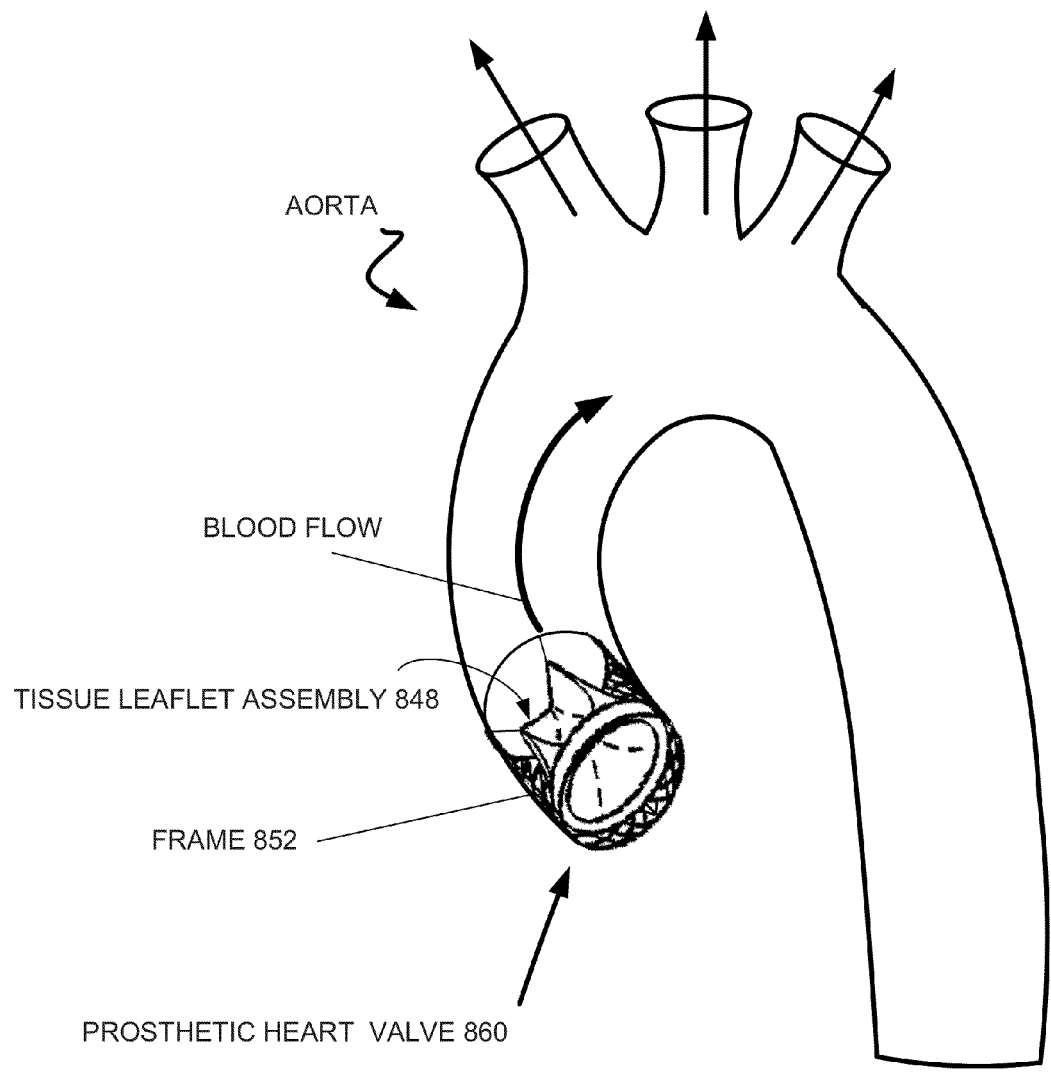
FIG. 16 is a schematic of a human aorta with the implanted prosthetic heart valve implanted at the site of the original diseased aortic valve.

Referring now to FIG. 7, a flow chart illustrating the general procedure associated with implantation of the percutaneously deliverable heart valve 860 is provided. More particularly, at 704, catheter access is gained to the patient's femoral artery and a guidewire is placed through the plane of the diseased valve that is targeted to receive the implant. FIG. 14 is a schematic of a simplified cutaway view of a human heart, including heart valves that may be targeted for receiving an embodiment of an implantable prosthetic heart valve. FIG. 15 illustrates the aorta with the guidewire placed through the diseased aortic valve. At 708, the percutaneously deliverable heart valve 860 in the form of a prepackaged assembled dry prosthetic heart valve is removed from the sterile packaging. The dry prosthetic heart valve assembly, including its lumens, are preferably flushed and prepared in the usual fashion for standard balloons and catheters that do not contain a biocompatible tissue. Advantageously, implantation of the dry prosthetic heart valve assembly can be conducted without specific maneuvers for rehydration of the tissue leaflet assembly 848 of the percutaneously deliverable heart valve 860. Some rehydration of the tissue leaflets may occur as a consequence of the routine flushing of the catheter lumens in preparation for use as with any other catheters. Additionally, implantation of the dry prosthetic heart valve assembly can proceed without additional cleaning steps, such as by having to use alcohol or water rinsing solutions. In addition, further mounting of the dry tissue leaflet assembly 848 that resides in the frame 852 of the percutaneously deliverable heart valve 860 is not needed, thereby obviating the need for another mounting step. Accordingly, the percutaneously deliverable heart valve 860 can essentially be implanted percutaneously in its dry state. At 712, the carrier catheter or balloon catheter is then coaxially mounted and advanced over the guidewire, such as under fluoroscopic vision initially to the level of the great vessel where it can be inspected under fluoroscopy. At 716, and after the nominal position and configuration is confirmed, the delivery system is advanced through the plane of the diseased valve under fluoroscopy, and the covering sheath is withdrawn, either at this point or during the advance prior to it, thus exposing the mounted implantable prosthetic heart valve 860 in place. At 720, in the case of a balloon expandable frame, and assuming the delivery approach involving the pre-mounting of the percutaneously deliverable heart valve 860 on the expansion balloon, the balloon is then inflated, deploying the percutaneously deliverable heart valve 860 in the plane of the valve. At 724, the leaflets of the percutaneously deliverable heart valve 860 operate immediately. The deployed prosthetic heart valve 860 is shown in FIG. 16, wherein the tissue leaflet assembly 848 serves to properly control the flow blood.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The one or more present inventions, in various embodiments, include components, methods, processes, systems and/or apparatus substantially as depicted and described herein, including various embodiments, subcombinations, and subsets thereof. Those of skill in the art will understand how to make and use the present invention after understanding the present disclosure.

The present invention, in various embodiments, includes providing devices and processes in the absence of items not depicted and/or described herein or in various embodiments hereof, including in the absence of such items as may have been used in previous devices or processes (e.g., for improving performance, achieving ease and/or reducing cost of implementation).

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

What is claimed is:

1. A method, comprising:
    partially compressing and mounting a prosthetic heart valve upon a delivery catheter, the prosthetic heart valve comprising a tissue;
    allowing the tissue to at least partially dry;
    further compressing and mounting the prosthetic heart valve upon the delivery catheter; and
    sterilizing and packaging the prosthetic heart valve and delivery catheter.

2. The method of claim 1, further comprising transporting the sterilized and packaged prosthetic heart valve and delivery catheter.

3. The method of claim 1, wherein the tissue comprises a treated pericardium tissue.

4. The method of claim 1, wherein prior to partially compressing and mounting the prosthetic heart valve upon the delivery catheter, the tissue is at least one of (a) not substantially dry, and (b) at least partially hydrated.

5. A method, comprising:
attaching a tissue to a frame;
partially compressing and mounting the frame, with the tissue attached thereto, upon a delivery catheter;
allowing the tissue to at least partially dry;
further compressing and mounting the frame, with the tissue attached thereto, upon the delivery catheter; and
sterilizing and packaging the frame and delivery catheter, with the tissue attached thereto.

6. The method of claim 5, wherein prior to partially compressing and mounting the frame, the tissue is at least one of (a) not substantially dry, and (b) at least partially hydrated.

7. The method of claim 5, further comprising transporting the sterilized and packaged frame, with the tissue attached thereto, mounted upon the delivery catheter, to a surgical or medical procedure facility.

8. The method of claim 5, wherein prior to attaching the tissue to the frame the tissue is folded to form a tissue leaflet assembly.

9. The method of claim 8, wherein the tissue leaflet assembly comprises at least one cuff and at least one pleat.

10. The method of claim 5, wherein the tissue comprises a treated pericardium tissue.

11. A method of preparing a percutaneous, trans-catheter prosthetic heart valve, comprising:
obtaining a membrane tissue from an organism;
treating the membrane tissue with at least one chemical to produce a treated membrane tissue;
drying the treated membrane tissue until it is a substantially dry tissue;
attaching the substantially dry tissue to a frame;
rehydrating the substantially dry tissue that is attached to the frame to form a rehydrated tissue;
collapsing the frame with the rehydrated tissue attached thereto; and
drying the rehydrated tissue attached to the collapsed frame until it is an again substantially dry tissue.

12. The method of preparing a percutaneous, trans-catheter prosthetic heart valve of claim 11, further comprising compressing and mounting the frame, with the again substantially dry tissue attached thereto, upon a delivery catheter.

13. The method of preparing a percutaneous, trans-catheter prosthetic heart valve of claim 12, further comprising sterilizing and packaging the frame, with the again substantially dry tissue attached thereto, mounted upon the delivery catheter.

14. The method of preparing a percutaneous, trans-catheter prosthetic heart valve of claim 13, further comprising at least one of transporting and shipping the sterilized and packaged frame with the again substantially dry tissue attached thereto, mounted upon the delivery catheter, to a surgical or medical procedure facility.

15. The method of preparing a percutaneous, trans-catheter prosthetic heart valve of claim 14, further comprising implanting the frame with the again substantially dry tissue attached thereto into a patient.

16. The method of preparing a percutaneous, trans-catheter prosthetic heart valve of claim 11, wherein the frame comprises a stent.

17. The method of preparing a percutaneous, trans-catheter prosthetic heart valve of claim 11, wherein prior to the attaching step the substantially dry tissue is not folded with a cuff and a pleat.

18. The method of preparing a percutaneous, trans-catheter prosthetic heart valve of claim 11, wherein prior to the attaching step the substantially dry tissue is folded to form a tissue leaflet assembly.

19. The method of preparing a percutaneous, trans-catheter prosthetic heart valve of claim 18, wherein the tissue leaflet assembly comprises at least one cuff and at least one pleat.

20. The method of preparing a percutaneous, trans-catheter prosthetic heart valve of claim 18, further comprising mounting the frame and the tissue leaflet assembly attached thereto upon a 12 to 14 French balloon catheter.

21. The method of preparing a percutaneous, trans-catheter prosthetic heart valve of claim 18, further comprising mounting the frame and the tissue leaflet assembly attached thereto upon a balloon catheter having a size of less than about 12 French.

22. The method of preparing a percutaneous, trans-catheter prosthetic heart valve of claim 18, further comprising mounting the frame and the tissue leaflet assembly attached thereto upon a balloon catheter having a size of between about 5 to 12 French.

23. The method of preparing a percutaneous, trans-catheter prosthetic heart valve of claim 18, further comprising mounting the frame and the tissue leaflet assembly attached thereto on a mandrel.

24. The method of preparing a percutaneous, trans-catheter prosthetic heart valve of claim 11, further comprising sterilizing the frame with the again substantially dry tissue attached thereto with exposure to at least one of ethylene oxide, a proton beam, and gamma radiation.

25. The method of preparing a percutaneous, trans-catheter prosthetic heart valve of claim 11, wherein said treating comprises immersion of the membrane tissue in a buffered or unbuffered 1-37.5% formalin solution for between about 3 days to 3 weeks.

26. The method of preparing a percutaneous, trans-catheter prosthetic heart valve of claim 11, wherein said treating comprises immersion of the membrane tissue in a buffered or unbuffered 1-37.5% formalin solution for between about 3 days to 5 weeks.

27. The method of preparing a percutaneous, trans-catheter prosthetic heart valve of claim 11, wherein said treating comprises immersion of the membrane tissue in a buffered or unbuffered 1-37.5% formalin solution containing at least one of free amino acids (a) lysine and (b) histidine, for between about 3 days to 3 weeks.

28. The method of preparing a percutaneous, trans-catheter prosthetic heart valve of claim 11, wherein said treating comprises immersion of the membrane tissue in a buffered or unbuffered 1-37.5% formalin solution containing at least one of free amino acids (a) lysine and (b) histidine, for between about 3 days to 5 weeks.

29. The method of preparing a percutaneous, trans-catheter prosthetic heart valve of claim 11, wherein said treating comprises immersion of the membrane tissue in 100% glycerol for greater than about 3 weeks.

30. The method of preparing a percutaneous, trans-catheter prosthetic heart valve of claim 11, wherein said treating comprises immersion of the membrane tissue in a 0.1-25% glutaraldehyde solution for between about 3 days to 3 weeks.

31. The method of preparing a percutaneous, trans-catheter prosthetic heart valve of claim 11, wherein said treating comprises immersion of the membrane tissue in a 0.1-25% glutaraldehyde solution for between about 3 days to 5 weeks.

32. The method of preparing a percutaneous, trans-catheter prosthetic heart valve of claim 11, wherein said treating comprises immersion of the membrane tissue in a 0.1-25% glutaraldehyde solution containing at least one of free amino acids (a) lysine and (b) histidine, for between about 3 days to 3 weeks.

33. The method of preparing a percutaneous, trans-catheter prosthetic heart valve of claim 11, wherein said treating comprises immersion of the membrane tissue in a 0.1-25% glutaraldehyde solution containing at least one of free amino acids (a) lysine and (b) histidine, for between about 3 days to 5 weeks.

34. The method of preparing a percutaneous, trans-catheter prosthetic heart valve of claim 11, wherein said treating comprises immersion of the membrane tissue in an oligomeric filtered 0.1-25% glutaraldehyde solution for between about 3 days to 3 weeks.

35. The method of preparing a percutaneous, trans-catheter prosthetic heart valve of claim 11, wherein said treating comprises immersion of the membrane tissue in an oligomeric filtered 0.1-25% glutaraldehyde solution for between about 3 days to 5 weeks.

36. The method of preparing a percutaneous, trans-catheter prosthetic heart valve of claim 11, wherein said treating comprises immersion of the membrane tissue in an oligomeric filtered 0.1-25% glutaraldehyde solution containing at least one of free amino acids (a) lysine and (b) histidine, for between about 3 days to 3 weeks.

37. The method of preparing a percutaneous, trans-catheter prosthetic heart valve of claim 11, wherein said treating comprises immersion of the membrane tissue in an oligomeric filtered 0.1-25% glutaraldehyde solution containing at least one of free amino acids (a) lysine and (b) histidine, for between about 3 days to 5 weeks.

38. The method of preparing a percutaneous, trans-catheter prosthetic heart valve of claim 11, wherein the membrane tissue comprises a pericardium tissue.

* * * * *